United States Patent
McNair

(10) Patent No.: US 11,749,404 B1
(45) Date of Patent: Sep. 5, 2023

(54) DECISION SUPPORT TOOL FOR VENOUS THROMBOEMBOLISM (VTE)

(71) Applicant: CERNER INNOVATION, INC., Kansas City, KS (US)

(72) Inventor: Douglas S. McNair, Leawood, KS (US)

(73) Assignee: Cerner Innovation, Inc., Kansas City, MO (US)

( * ) Notice: Subject to any disclaimer, the term of this patent is extended or adjusted under 35 U.S.C. 154(b) by 936 days.

(21) Appl. No.: 16/596,227

(22) Filed: Oct. 8, 2019

Related U.S. Application Data

(60) Provisional application No. 62/742,470, filed on Oct. 8, 2018.

(51) Int. Cl.
| | |
|---|---|
| *G16H 50/20* | (2018.01) |
| *G06N 5/045* | (2023.01) |
| *G16B 40/00* | (2019.01) |
| *G06N 20/00* | (2019.01) |

(52) U.S. Cl.
CPC ............ *G16H 50/20* (2018.01); *G06N 5/045* (2013.01); *G16B 40/00* (2019.02); *G06N 20/00* (2019.01)

(58) Field of Classification Search
None
See application file for complete search history.

(56) References Cited

U.S. PATENT DOCUMENTS

| | | | |
|---|---|---|---|
| 9,922,285 B1 | 3/2018 | Glode et al. | |
| 2014/0056889 A1* | 2/2014 | Morimoto | A61P 19/02 435/6.12 |
| 2017/0027498 A1 | 2/2017 | Larson et al. | |
| 2018/0039732 A1 | 2/2018 | Szeto et al. | |
| 2019/0355438 A1* | 11/2019 | Venn | G16B 40/00 |

OTHER PUBLICATIONS

Pre interview First Office Action received for U.S. Appl. No. 16/595,073, dated Oct. 26, 2022, 6 pages.

(Continued)

*Primary Examiner* — William C Trapanese
(74) *Attorney, Agent, or Firm* — Invoke

(57) ABSTRACT

An improved decision support tool is provided for detecting and treating human patients at risk for having (or developing) venous thromboembolism VTE. The tool determines a quantitative probability of VTE by utilizing a smart sensor based on a particular machine-learning model for detecting specific biomarkers determined to be related to VTE. In particular, a quantitative probability of VTE may be determined via a model based on interrelationships between multiple components of the human body's complement cascade and their coupling to coagulation processes. In one aspect, a quasi-Dirichlet distribution "mixture" relationship between total hemolytic complement (CH50) activity and complement protein C3 levels is employed as part of a smart sensor and decision support tool to provide predictive, diagnostic, and prognostic applications and for guiding prevention and treatment of acute VTE. Where the smart sensor determines a risk for VTE, then the decision support tool may initiate an intervening action.

26 Claims, 17 Drawing Sheets

CH50, C3, AND C4 EXPERIENCE DIFFERENTIAL CHANGES IN VTE

(56) References Cited

OTHER PUBLICATIONS

Iuliana et al., "Sequence Kernel Association Tests for the Combined Effect of Rare and Common Variants", The American Journal of Human Genetics 92, Available online at <https://www.cell.com/ajhg/pdf/S0002-9297(13)00176-6.pdf>, Jun. 6, 2013, pp. 841-853.

Kelley et al., "Basset: Learning the Regulatory Code of the Accessible Genome with Deep Convolutional Neural Networks", Cold Spring Harbor Laboratory Press, Available online at <https://genome.cshlp.org/content/early/2016/05/03/gr.200535.115.full.pdf>, May 3, 2016, pp. 990-999.

Penco et al., "Assessment of the Role of Genetic Polymorphism in Venous Thrombosis Through Artificial Neural Networks", Annals of Human Genetics, University College London, Available online at <https://onlinelibrary.wiley.com/doi/epdf/10.1111/j.1529-8817.2005.00206.x>, Jul. 26, 2005, pp. 693-706.

\* cited by examiner

| PATIENT... | ENTER |
|---|---|
| CH50 | 202 |
| C3 | 55 |
| C4 | 34.0 |

| EVALUATE | RESULTS |
|---|---|
| DATA COMPLETE? | YES |
| LIKELIHOOD OF VTE IS... | LOW 5% |

900

```
# Coefficient      beta      SE         z       p-value
# (Intercept)      6.979    1.015    6.873   6.30e-12 ***
# logit_ch50      -7.600    1.461   -5.201   1.98e-07 ***
# log10(c4c3ratio) 12.182   1.971    6.181   6.37e-10 ***
```

| PATIENT... | ENTER |
|---|---|
| CH50 | 190 |
| C3 | 46 |
| C4 | 40.0 |

| EVALUATE | RESULTS |
|---|---|
| DATA COMPLETE? | YES |
| LIKELIHOOD OF VTE IS... | MODERATE TO HIGH 25% |

```
# Coefficient        beta       SE       z      p-value
# (Intercept)       6.979    1.015   6.873  6.30e-12 ***
# logit_ch50       -7.600    1.461  -5.201  1.98e-07 ***
# log10(c4c3ratio) 12.182    1.971   6.181  6.37e-10 ***
```
950

*FIG. 9B.*

| ITEM | VALUE |
|---|---|
| SENSITIVITY | 99% |
| SPECIFICITY | 95% |
| EVENT PREVALENCE | 50% |
| POSITIVE PREDICTIVE VALUE (PPV) | 95% |
| NEGATIVE PREDICTIVE VALUE (NPV) | 99% |

*FIG. 10.*

```
###########################################################################

#   Dirichlet regression and logistic regression of postmenopausal women's complement
#   levels, with and without VTE

##################################################################### library(Hmisc) # needed for na.delete() function
library(rgl)
library(miscTools)
library(Formula)
library(maxLik)
library(DirichletReg)

# define function to force normalization of ch50 and c3 to 1.00 as though they were a Dirichlet mixture
dir.norm <- function (Y, trafo = sqrt(.Machine$double.eps), base = 1, norm_tol = sqrt(.Machine$double.eps))
{
    force.norm <- FALSE
    state.tran <- FALSE
    force.tran <- FALSE
    if (any(is.na(Y))) {
        Y[which(rowSums(is.na(Y)) > 0), ] <- NA
    }
    if (any(na.delete(Y) < 0))
        stop("\"Y\" contains values < 0.")
    Y.original <- Y
    if ((!is.matrix(Y) && !is.data.frame(Y)) || ifelse(is.null(ncol(Y)),
        FALSE, ncol(Y) == 1L)) {
        if (any((na.delete(Y) < 0) || (na.delete(Y) > 1))) {
            stop("only one variable supplied with values outside [0, 1].\nbeta distribution cannot safely be
assumed.\nprepare data first.")
        }
        Y <- cbind(1 - Y, Y)
        .name <- deparse(match.call()$Y)
        .name <- gsub(".*\\$", "", .name)
        .name <- gsub("\\[.*", "", .name)
        if (length(.name) == 0L)
            .name <- "Y"
        colnames(Y) <- c(paste("1 -", .name), .name)
        message("only one variable in [0, 1] supplied - beta-distribution assumed.\ncheck this assumption.")
    }
    if (!is.matrix(Y) && !is.data.frame(Y))
        stop("\"Y\" must be either a matrix or a data.frame.")
    if (ncol(Y) <= 1)
        stop("\"Y\" must at least have two columns.")
    if ((base < 1) || (base > ncol(Y)))
        stop("\"base\" must be in the range of variables.")
    if ((base%%1) != 0)
        stop("\"base\" must be an integer value.")
    if (is.na(trafo) || (is.numeric(trafo) && ((length(trafo) !=
        1L) || (trafo < 0) || (trafo >= 0.5)))) {
        stop("\"trafo\" must either be a logical or a (small) numeric value > 0. See ?DR_data")
    }
```

⋮

CONTINUES IN FIG. 11B

*FIG. 11A.*

. CONTINUES FROM FIG. 11A

```
if (is.null(colnames(Y)))
    colnames(Y) <- paste0("v", seq_len(ncol(Y)))
row.sums <- rowSums(Y)
if (!isTRUE(all.equal(na.delete(row.sums), rep(1, length(na.delete(row.sums))),
    tolerance = norm_tol, check.attributes = FALSE))) {
    Y <- Y/row.sums
    force.norm <- TRUE
}
if ((is.logical(trafo) && trafo) || (is.numeric(trafo) &&
    any(na.delete(Y) < trafo, na.rm = TRUE) || any(na.delete(Y) >
    (1 - trafo), na.rm = TRUE))) {
    n.obs <- length(na.delete(row.sums))
    Y <- (Y * (n.obs - 1) + 1/ncol(Y))/n.obs
    state.tran <- TRUE
    if (is.logical(trafo) && trafo) {
        force.tran <- FALSE
    }
    else {
        force.tran <- TRUE
    }
}
if (any(na.delete(Y) <= 0, na.rm = TRUE) || any(na.delete(Y) >=
    1, na.rm = TRUE)) {
    stop("\"trafo\" was suppressed, yet values on the boundary of the support are present (0 and 1).\nConsider setting \"trafo\" = TRUE or to a threshold.\nSee ?DR_data")
}
res <- structure(as.matrix(Y), Y.original = as.data.frame(Y.original),
    dims = ncol(Y), dim.names = colnames(Y), obs = nrow(Y),
    valid_obs = length(na.delete(row.sums)), normalized = force.norm,
    transformed = state.tran, base = base, class = "DirichletRegData")
if (force.norm && force.tran) {
    warning("not all rows sum up to 1 => normalization forced\n  some entries are 0 or 1 => transformation forced",
        immediate. = TRUE)
}
else if (force.norm) {
    warning("not all rows sum up to 1 => normalization forced",
        immediate. = TRUE)
}
else if (force.tran) {
    warning("some entries are 0 or 1 => transformation forced",
        immediate. = TRUE)
}
return(res)
} load data (30 cases, 5 vars)
dat <- read.csv(file="c:/0_cerdsm/IP/VTE/vte.csv", header=TRUE,
        colClasses=c("character", rep("integer",3), rep("numeric",4)))
# id, vte, ch50, c3,   c4,   c3c4t, c3fr_c3c4t,    c4c3ratio
#       U/mL  mg/dL mg/dL total  fraction of total
```

*FIG. 11B.*

CONTINUES IN FIG. 11C

CONTINUES FROM FIG. 11B

```
dat$Smp <- dir.norm(dat[, 3:4])  # forces normalization in case not all rows' sums = 1.00 even though ch50 and c3 are in different units head(dat)
id vte ch50 c3  c4 c3c4t c3fr_c3c4t c4c3ratio Smp.ch50  Smp.c3
# 194499003  0   68 178 35.6 213.6   0.833     0.200  0.2764228 0.7235772
# 179823666  0  131 129 34.0 163.0   0.791     0.264  0.5038462 0.4961538
# 195060495  0  118  69  9.0  78.0   0.885     0.130  0.6310160 0.3689840
# 173496151  0   84 140 38.0 178.0   0.787     0.271  0.3750000 0.6250000
# 173522338  0   74 114 33.0 147.0   0.776     0.289  0.3936170 0.6063830
181682185  0  113 103 26.0 129.0   0.798     0.252  0.5231481 0.4768519 perform scaling of variables as fraction of "full-scale" values check to see whether normalization step is sensitive to c3 and ch50 units of measure
dat$c3.300 <- dat$c3/300
dat$ch50.300 <- dat$ch50/300
dat$Smp.300 <- dir.norm(dat[, 10:11])  # forces normalization in case not all rows' sums = 1.00 even though ch50 and c3 are in different units
head(dat)
#        id vte ch50 c3  c4 c3c4t c3fr_c3c4t c4c3ratio Smp.ch50  Smp.c3    c3.300   ch50.300  Smp.300.c3.300 Smp.300.ch50.300
# 194499003  0   68 178 35.6 213.6  0.833    0.200  0.2764228 0.7235772 0.5933333 0.2266667    0.7235772       0.2764228   same as orig normalizatn
# 179823666  0  131 129 34.0 163.0  0.791    0.264  0.5038462 0.4961538 0.4300000 0.4366667    0.4961538       0.5038462
# 195060495  0  118  69  9.0  78.0  0.885    0.130  0.6310160 0.3689840 0.2300000 0.3933333    0.3689840       0.6310160
# 173496151  0   84 140 38.0 178.0  0.787    0.271  0.3750000 0.6250000 0.4666667 0.2800000    0.6250000       0.3750000
# 173522338  0   74 114 33.0 147.0  0.776    0.289  0.3936170 0.6063830 0.3800000 0.2466667    0.6063830       0.3936170
# 181682185  0  113 103 26.0 129.0  0.798    0.252  0.5231481 0.4768519 0.3433333 0.3766667    0.4768519       0.5231481
conclude that the dir.norm() function is not sensitive to scale or unites of measure determine Dirichlet regression model, base = elt denoting base variable in mixture
mod1 <- DirichReg(Smp ~ vte | 1, data=dat, model = "alternative", base=1)   # conditioned on nothing
mod2 <- DirichReg(Smp ~ vte | vte, data=dat, model = "alternative", base=1) # conditioned on vte as instrumental variable
anova(mod1, mod2)
#      Deviance  N. par Difference df Pr(>Chi)
# Model 1 -964.90    3
# Model 2 -966.26    4     1.3584   1   0.2438
# conclude two models are comparably accurate
```

FIG. 11C.

CONTINUES IN FIG. 11D

CONTINUES FROM FIG. 11C

```
summary(mod1)
# Coefficients for variable no. 2: c3
#           Estimate Std. Error z value Pr(>|z|)
# (Intercept)  0.01711  0.01865  0.917   0.359
# vte        -1.02636  0.04862 -21.108  <2e-16 ***
# ------------------------------------------------------------------
# PRECISION MODEL:
# ------------------------------------------------------------------
#           Estimate Std. Error z value Pr(>|z|)
(Intercept) 3.29408  0.06215    53    <2e-16 *** plot differences of categories
par(mfrow = c(1, 2), mar = c(2, 2, 2, 2) + 0.25)
for (i in 1:2) {
  boxplot(dat$Smp[, i] ~ dat$vte, ylim = range(dat$Smp[, 1:2]), main=paste(names(dat)[i+3]), xlab="Condition", ylab="Proportion")
  segments(c(-5, 1.5), unique(fitted(mod2)[, i]), c(1.5, 5), unique(fitted(mod2)[,i]), lwd=2, lty=2)
} perform classification of new cases using second model
alpha <- predict(mod2, data.frame(vte = factor(c("0", "1"))), F, T, F)
L <- sapply(1:2, function(i) ddirichlet(DR_data(dat[31:36, 1:4]), unlist(alpha[i, ])))
LP <- L/rowSums(L)
dimnames(LP) <- list(paste("C", 1:6), c("0", "1"))
print(data.frame(round(LP*100, 1), pred. = as.factor(ifelse(LP[, 1] > LP[, 2], "==> 0", "==> 1"))), print.gap = 2)
# 1  59.4  40.6  ==> A
# 2  43.2  56.8  ==> B
# 3  38.4  61.6  ==> B
# 4  43.8  56.2  ==> B
# 5  36.6  63.4  ==> B
6  70.2  29.8  ==> A determine logistic regression models mod3 <- glm(vte ~ Smp + c4c3ratio, data=dat, family=binomial)
summary(mod3)
# Coefficients: (1 not defined because of singularities) ************* best AIC but data are ill-conditioned in this
#    pilot cohort of women
#           Estimate Std. Error z value Pr(>|z|)
# (Intercept) -19.567   2.445  -8.003 1.22e-15 ***
# Smpch50      21.746   3.422   6.355 2.09e-10 ***
# Smpc3         NA       NA     NA      NA
# c4c3ratio    14.426   2.605   5.537 3.07e-08 ***
# ---
Null deviance: 468.35  on 499  degrees of freedom
# Residual deviance: 106.99  on 497  degrees of freedom
# AIC: 112.99
```

*FIG. 11D.*

CONTINUES IN FIG. 11E

CONTINUES FROM FIG. 11D

```
mod4 <- glm(vte ~ ch50 + c4c3ratio, data=dat, family=binomial)
summary(mod4)
# Coefficients:
Estimate Std. Error z value Pr(>|z|)
# (Intercept) -14.024149  1.626027  -8.625  < 2e-16 ***
# ch50          0.042042  0.007129   5.898 3.69e-09 ***
# c4c3ratio    20.019349  2.586667   7.739 9.99e-15 ***
# ---
Null deviance: 468.35  on 499  degrees of freedom
# Residual deviance: 145.49  on 497  degrees of freedom
AIC: 151.49 mod5 <- glm(vte ~ log10(ch50) + log10(c4c3ratio), data=dat, family=binomial)
summary(mod5)
# Coefficients:
Estimate Std. Error z value Pr(>|z|)
# (Intercept)        -20.867      4.563  -4.573 4.81e-06 ***
# log10(ch50)         13.001      2.276   5.713 1.11e-08 ***
# log10(c4c3ratio)    16.951      2.217   7.645 2.08e-14 ***
# ---
Null deviance: 468.35  on 499  degrees of freedom
# Residual deviance: 137.58  on 497  degrees of freedom
AIC: 143.58 mod6 <- glm(vte ~ log10(c4c3ratio), data=dat, family=binomial)
summary(mod6)
# Coefficients:
Estimate Std. Error z value Pr(>|z|)
# (Intercept)         6.2674     0.8388   7.472 7.9e-14 ***
# log10(c4c3ratio)   15.6100     1.7437   8.952 < 2e-16 ***
# ---
Null deviance: 468.35  on 499  degrees of freedom
# Residual deviance: 189.01  on 498  degrees of freedom
AIC: 193.01 try fractional logit transformation
dat$logit_c3 <- exp(5.66 - 0.054*dat$c3)/(1 + exp(5.66 - 0.054*dat$c3))
dat$logit_ch50 <- exp(-4.81 + 0.043*dat$c3)/(1 + exp(-4.81 + 0.043*dat$c3))

mod7 <- glm(vte ~ logit_ch50 + log10(c4c3ratio), data=dat, family=binomial)
summary(mod7)
# Coefficients:                        ************* adequate AIC in this pilot cohort of women
#                   Estimate Std. Error z value Pr(>|z|)
# (Intercept)         6.979      1.015   6.873 6.30e-12 ***
# logit_ch50         -7.600      1.461  -5.201 1.98e-07 ***
# log10(c4c3ratio)   12.182      1.971   6.181 6.37e-10 ***
# ---
Null deviance: 468.35  on 499  degrees of freedom
# Residual deviance: 132.12  on 497  degrees of freedom
# AIC: 138.12
# conclude that this model is acceptable substitute for mod3 in situations when Dirichlet regression
#    is unstable (singularities in optimization)
```

FIG. 11E.

DECISION SUPPORT TOOL FOR VENOUS THROMBOEMBOLISM (VTE)

BACKGROUND

Venous thrombosis and venous thromboembolism (VTE), usually evolving from thrombophilia and commonly manifested as deep venous thrombosis (DVT) and pulmonary embolism (PE), are a major health concern worldwide. There are many phenotypic and demographic risk factors, but there are also many known strong genetic risk factors for VTE. These involve deficiencies in the innate anticoagulants protein C, protein S and anti-thrombin.

Venous thromboembolism (VTE) is a common and potentially fatal condition in postmenopausal women. In particular, VTE has emerged as the most prevalent adverse effect of oral estrogens (hormone replacement therapy, or HRT) in 50- to 65-year-old women. It is estimated that VTE affects between 100,000 and 150,000 postmenopausal women each year in the U.S. By contrast, menopause confers increased risk of atherosclerosis and other vascular events, such as venous thromboembolism and the duration of exposure to the elevated risk lasts decades.

Some treatments may be less effective, depending on conditions of the patient. For example, traditional treatments, such as anticoagulants, are not particularly effective in preventing VTE in menopause. Many treatment options can be quite expensive, and may not be needed in certain instances. For example, eculizumab (Alexion Soliris®), which is a monoclonal antibody that is currently used in paroxysmal nocturnal hematuria (PNH), may be effective in preventing post-menopausal VTE whose origin includes complement activation. Eculizumab is currently very expensive (400,000/yr AWP). Therefore, a decision support tool, such as provided herein, for more accurately and quantitatively identifying those women in whom use of such medications would be medically appropriate and cost-efficacious is valuable.

SUMMARY

This summary is provided to introduce a selection of concepts in a simplified form that are further described below in the detailed description. This summary is not intended to identify key features or essential features of the claimed subject matter, nor is it intended to be used in isolation as an aid in determining the scope of the claimed subject matter.

Technologies described herein provide an improved decision support tool for detecting and treating human patients at risk for having (or developing) VTE. A decision support tool determines a quantitative probability of VTE by utilizing a smart sensor that is based on a particular machine-learning model for detecting one or more specific biomarkers determined to be related to venous thromboembolism (VTE). In particular, a quantitative probability of VTE may be determined via a machine-learning classification or prediction model of interrelationships between multiple components of the human body's complement cascade and their coupling to coagulation processes. Complement proteins are part of the body's inflammatory processes and are elevated in contexts that involve inflammation, tissue injury, tissue repair, and infection.

According to an embodiment, a quasi-Dirichlet distribution "mixture" relationship between total hemolytic complement (CH50) activity and complement protein C3 levels is employed as part of a smart sensor. Levels of CH50 and C3 are determined and mathematically transformed so as to be normalized to sum to 1. When this transformation is performed, the transformed normalized CH50 and C3 values bear a strong statistical association to the subsequent occurrence of newly-incident VTE and to the diagnosis of VTE that has already occurred acutely. Thus, when the relative level of CH50 rises, the relative level of C3 tends to fall as circulating C3 is consumed by the complement activation process more rapidly than the liver is able to synthesize more C3 to replenish or sustain baseline levels of C3. As such, the quasi-Dirichlet relationship between normalized CH50 and C3 may be utilized by the smart sensor and decision support tool to provide predictive, diagnostic, and prognostic applications and for guiding prevention and treatment of acute VTE. In one embodiment, where the smart sensor application determines a risk for VTE, then the decision support tool may initiate an intervening action, such as issuing a notification or alert, scheduling healthcare resources, or generating or modifying a care plan for the patient.

BRIEF DESCRIPTION OF THE DRAWINGS

The present invention is described in detail below with reference to the attached drawing figures, wherein:

FIGS. 9A and 9B depict example graphical user interfaces of a decision support tool for predicting or diagnosing risk of VTE in a human patient, in accordance with an embodiment of the disclosure;

FIG. 10 depicts statistical performance of the example embodiment of the present disclosure actually reduced to practice and described in connection to FIG. 2; and FIGS. 11A-11E illustratively provide an example embodiment of computer program routines for implementing a practical application of the smart sensor for detecting or predicting VTE risk, which was actually reduced to practice and described in connection to FIG. 2.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of our invention may be embodied as, among other things: a method, system, or set of instructions embodied on one or more computer readable media, which is described herein. Accordingly, the embodiments may take the form of a hardware embodiment, a software embodiment, or an embodiment combining software and hardware. In one embodiment, the invention takes the form of a computer-program product that includes computer-usable instructions embodied on one or more computer readable media.

At a high level, this disclosure describes, among other things, technologies for an improved decision support tool for detecting and treating human patients at risk for having (or developing) VTE. A decision support tool determines a quantitative probability of VTE by utilizing a smart sensor that is based on a particular machine-learning model for detecting one or more specific biomarkers determined to be related to venous thromboembolism (VTE). In some embodiments, statistical dependencies among biomarkers related to venous thromboembolism (VTE) may be determined and certain mathematical transformations may be performed upon the biomarkers' values such that differential changes among them that are antecedent to and concomitant with VTE may be accentuated so as to be more reliable indicators of VTE risk thereby functioning as a smart sensor. Further, in some embodiments, the smart sensor comprises a multivariable classification/prediction model, which may be established and/or trained based on the transformed values, and then subsequently utilized in a decision support tool to determine for a new set of input biomarker values and for determining whether the values merit decision-making and intervening action and, if so, to provide quantitative interpretations and electronic communication thereof.

Figure 3:
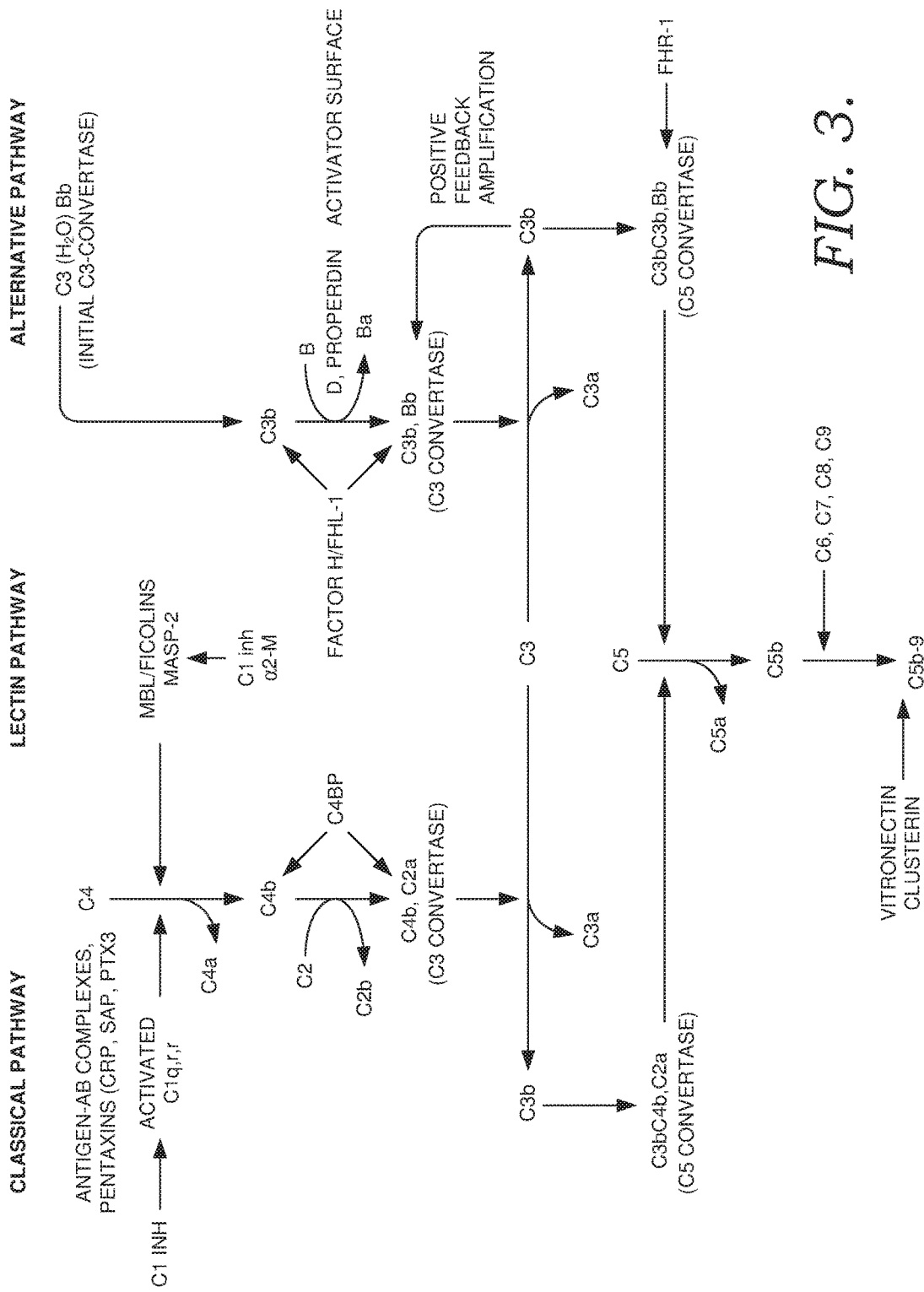
FIG. 3 depicts aspects of the inflammatory process showing the complement protein system and assays for a human person.
Figure 4:
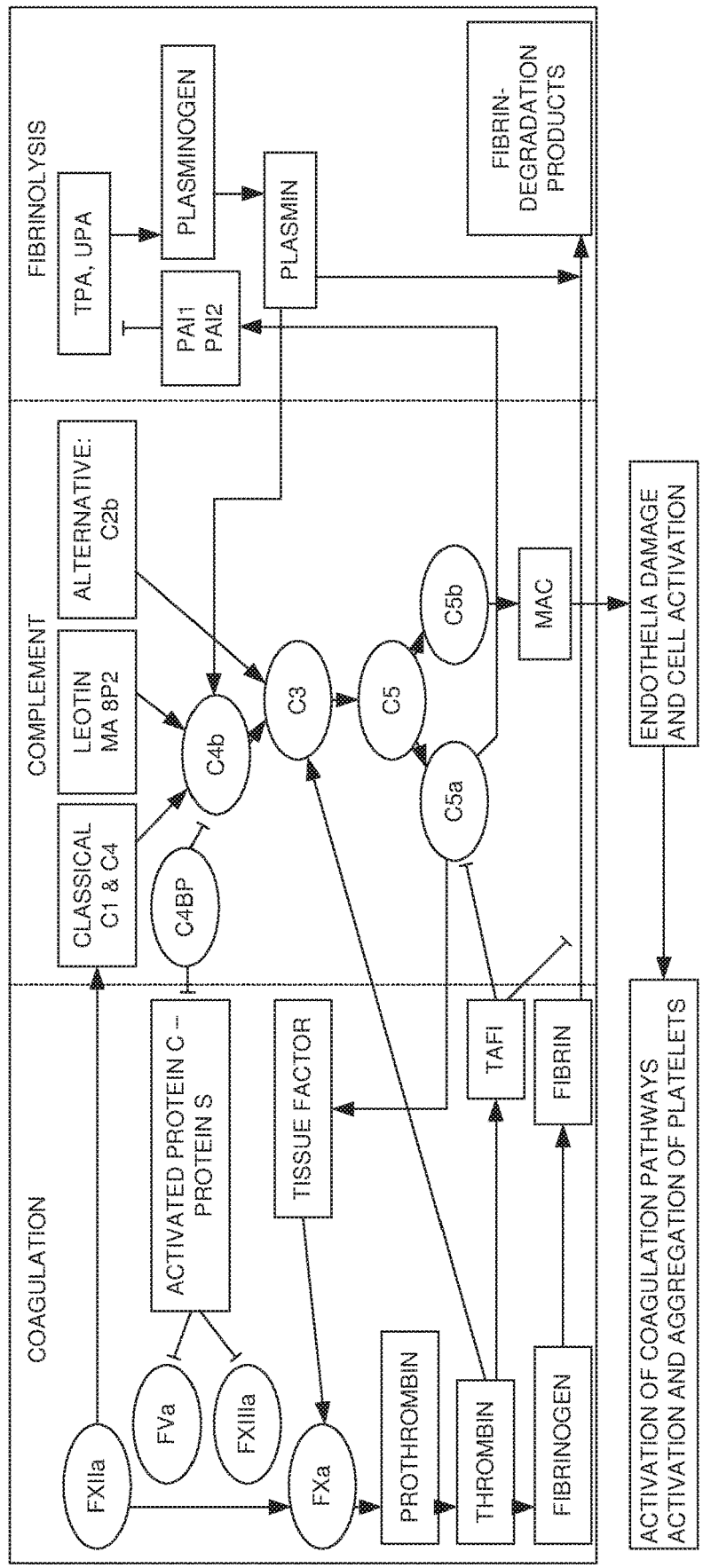
FIG. 4 depicts a flow chart characterizing the biochemistry of coagulation, with regards to an example embodiment described in connection to FIG. 2.

In some embodiments, the smart sensor's machine-learning classification or prediction model utilizes interrelationships between multiple components of the human body's complement cascade and their coupling to coagulation processes. An example of the coagulation process is illustratively provided in FIG. 4. Complement is a system of approximately 31 cell membrane and plasma proteins. C1 triggers activation of C4, which in turn activates C2, C3, C5, and other complement species. Once a complement cascade is activated, the proteins interact with each other in several pathways. The "classical" pathway is triggered by antigen-antibody complexes and includes all complement proteins (C1 through C9, or "total complement" CH50). The "alternate" pathway occurs when C3, C5, and C9 are activated without participation of C1, C2, and C4. Complement proteins are part of the body's inflammatory processes and are elevated in contexts that involve inflammation, tissue injury, tissue repair, and infection, such as shown in FIG. 3.

Ordinarily complement C3 comprises 70% to 80% of total circulating complement in the blood plasma. The acute-phase process in response to inflammatory processes generally causes an increase in production of C3 by the liver, resulting in higher-than-normal levels of circulating C3 during acute and chronic inflammation. However, an inflammatory process that is ongoing may cause C3 to be consumed faster than more C3 is produced, such that circulating C3 levels may be decreased compared to normal levels. C4 may also be increased in the acute-phase response but the circulating C4 level is likewise subject to imbalance in the rate of production compared to the rate of ongoing consumption of C4. Both C3 and C4 are quantitatively measured by immunoturbidimetry (units: mg/dL).

Total hemolytic complement (CH50) is measured as a functional activity by enzyme immunoassay or by lysis of sheep red blood cells (units: U/mL) and, when the complement cascade has been activated, may exhibit increased values even when quantitative levels of circulating C3 or other complement components have been depleted by ongoing consumption in the inflammatory process. Under ordinary conditions, CH50 total complement in adults is in the range 41 to 90 U/mL. In postmenopausal women, circulating C3 levels are normally between 88 mg/dL to 206 mg/dL, and C4 levels range from 13 mg/dL to 75 mg/dL. In times of illness there may or may not be an absolute change in total complement, depending on the status of comorbid illnesses, inflammation, and treatments of these.

Figure 6:
FIGS. 6, 7, and 8 depict aspects of the relationship between C50, C3, and C4 showing differential changes in VTE.
Figure 7:
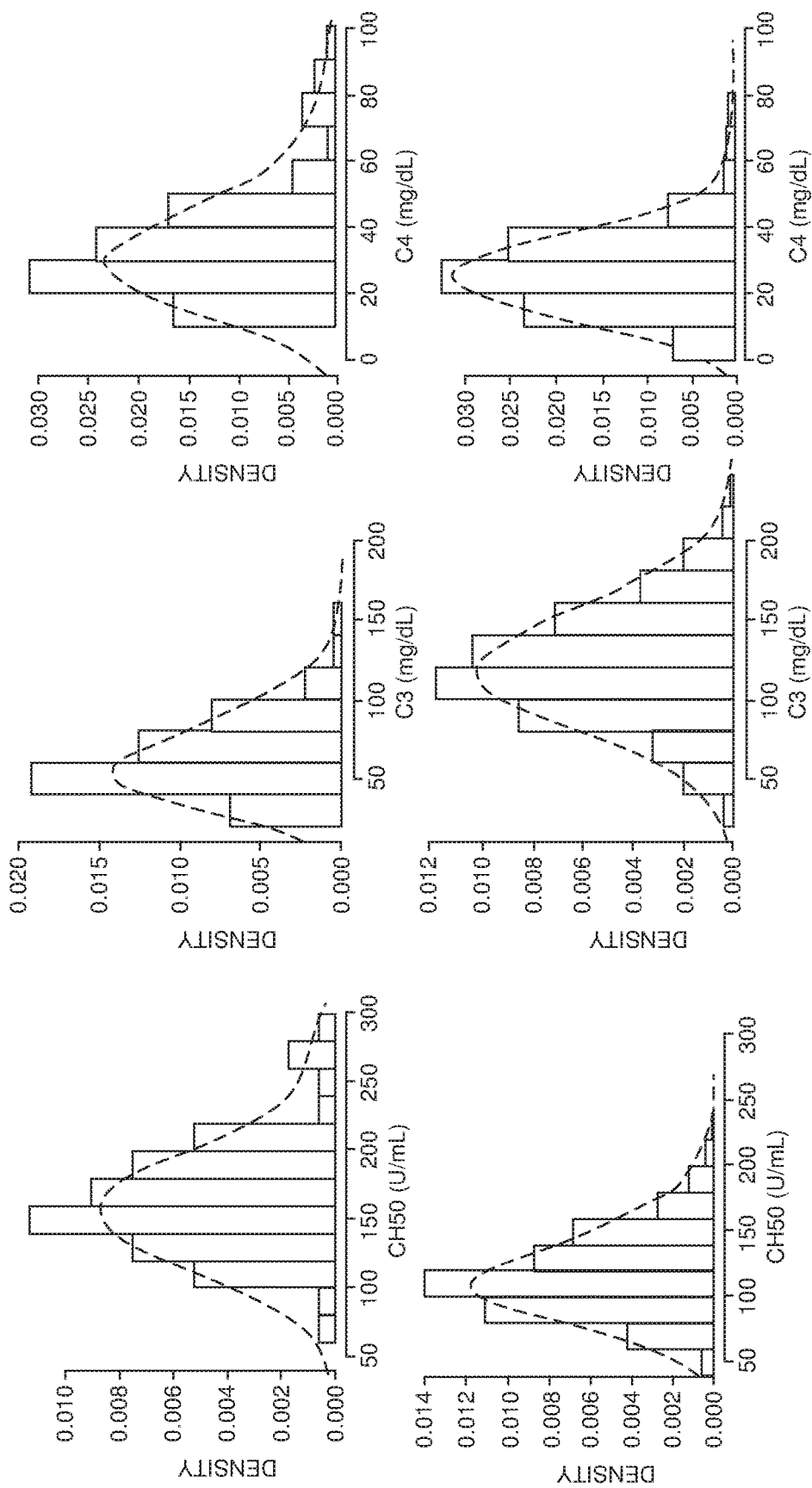
Figure 8:
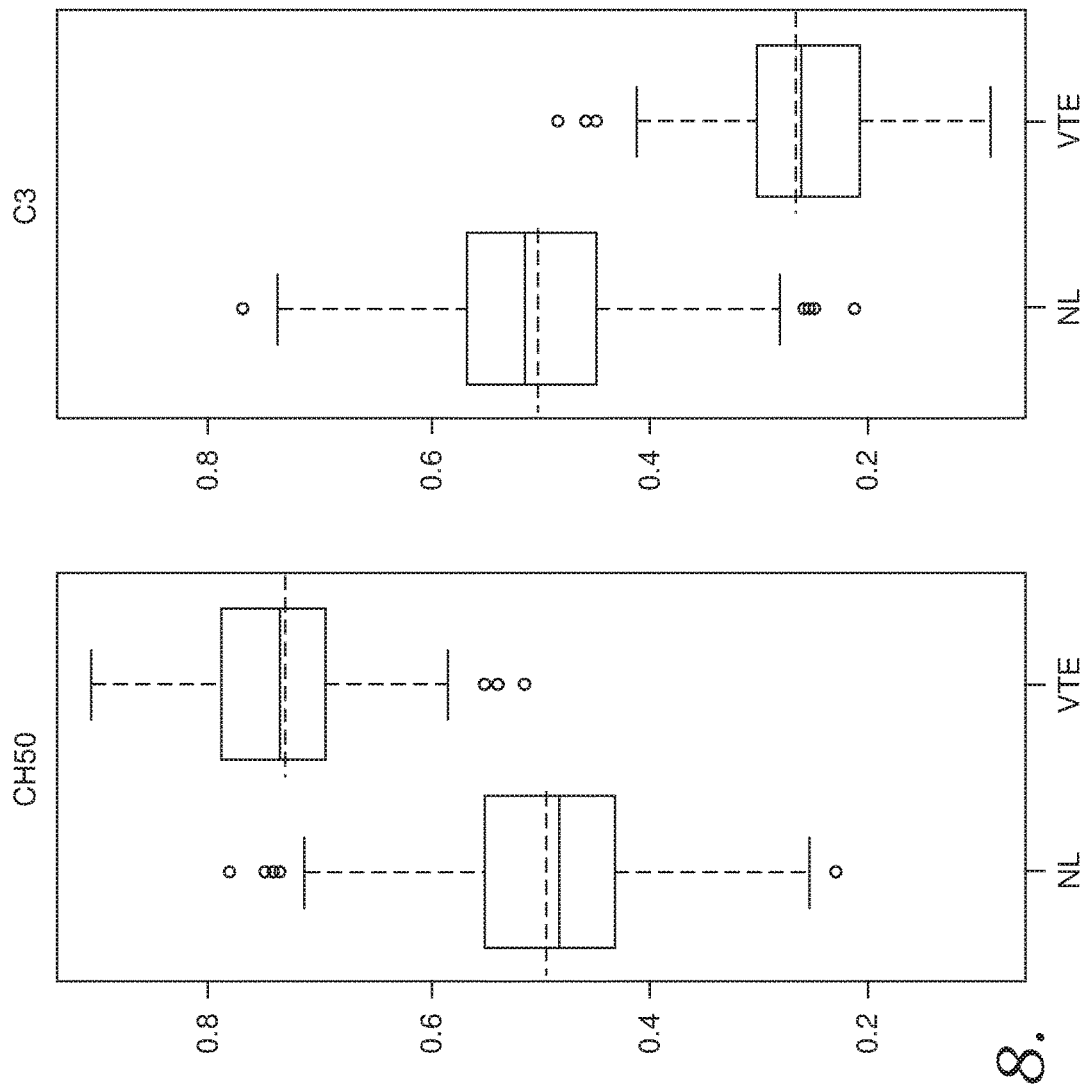

However, the inventor of the embodiments described herein has discovered that there is usually a relative CH50 activity and relative concentrations of C3 and C4 in the period preceding and shortly following a VTE event. In postmenopausal women, it is known that C3 levels are associated with menopausal status and increased plasminogen activator inhibitor-1 (PAI-1) and tissue plasminogen activator antigen (tPA-Ag) levels. In postmenopausal women, elevated C4 is associated with increased coagulation Factor VII and fibrinogen levels, both of which are central in the coagulation cascade. FIGS. 6, 7, and 8 depict relationships of C3, C4, and CH50 showing that these variables experience differential changes in patients having or at risk for VTE.

A novel, heretofore unknown aspect of the embodiments described herein is the quasi-Dirichlet distribution "mixture" relationship between CH50 activity and C3 levels in the context of incipient thromboembolism or acute materialized thromboembolism. While the absolute levels of CH50 activity and C3 concentration do not necessarily sum to exactly one as in classical Dirichlet-distributed mixture components, the levels of CH50 and C3 can be mathematically transformed so as to be normalized to sum to 1. When this transformation is performed, the transformed normalized CH50 and C3 values bear a strong statistical association to the subsequent occurrence of newly-incident VTE and to the diagnosis of VTE that has already occurred acutely. When the relative level of CH50 rises, the relative level of C3 tends to fall as circulating C3 is consumed by the complement activation process more rapidly than the liver is able to synthesize more C3 to replenish or sustain baseline levels of C3. As such, the quasi-Dirichlet relationship between normalized CH50 and C3 can serve in predictive, diagnostic, and prognostic applications to guide prevention and treatment of acute VTE.

Figure 5:
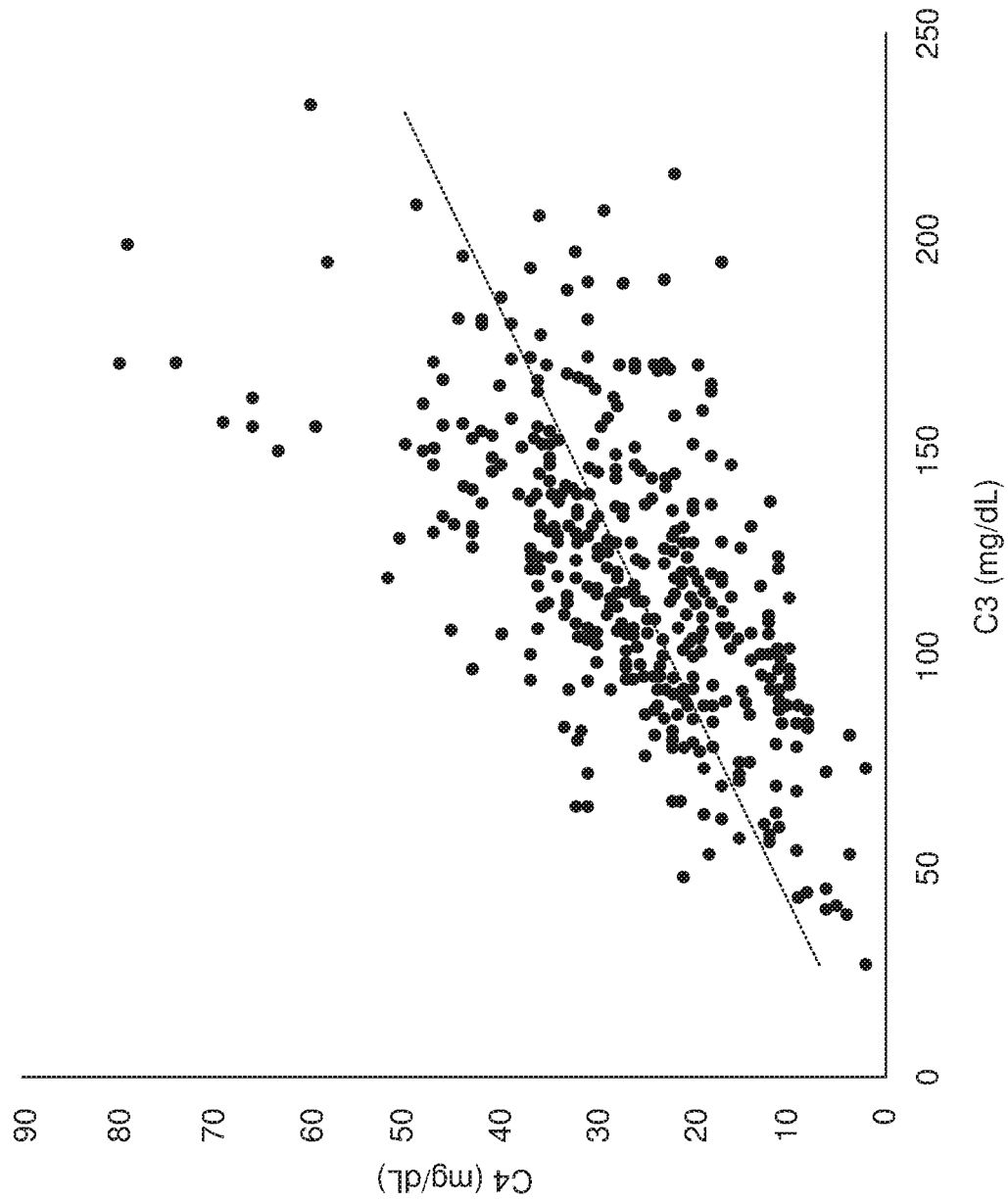
FIG. 5 depicts aspects of a logistic regression showing C2-C4 complement production and consumption, in accordance with an embodiment of the disclosure.

A further novel aspect of the embodiments disclosed herein is the discovery of a statistical relationship between complement components C3 and C4 in the context of emerging VTE. FIG. 5 depicts compliment production and consumption of C3 and C4, showing the relationship. C4 is ordinarily a minor component comprising a small percentage of circulating complement. However, in the setting of acute thrombosis and thromboembolism, synthesis of C4 is up-regulated and circulating levels of C4 tend to increase. Given that absolute C3 level is frequently decreasing in this setting as noted above, the ratio of C4 to C3 tends to increase substantially. A logarithmic transformation or other suitable transformation of the dimensionless C4/C3 ratio serves to reduce the effects of within-person specimen-to-specimen variability in C3 and C4 levels, pre-analytic variability arising in specimen transport and storage, and of analytic imprecision of the immunoturbidimetric C3 and C4 assays.

As described above, (VTE), usually evolving from thrombophilia and commonly manifested as deep venous thrombosis (DVT) and pulmonary embolism (PE), is a major health concern worldwide. VTE is a common and potentially fatal condition in postmenopausal women. In particular, VTE has emerged as the most prevalent adverse effect of oral estrogens (hormone replacement therapy, or HRT) in 50- to 65-year-old women. Obesity and VTE history can be used to identify women at elevated risk but genetic screening is currently not often performed and may not be cost-effective. The risk of venous thromboembolism (VTE) varies throughout a woman's life and is associated primarily with hormonal exposure. Alteration in hemostatic mechanisms, including resistance to activated protein C, may explain this altered risk. Initially, development of VTE with the use of oral contraceptives in young adulthood may reveal inherited thrombophilia. Pregnancy, and particularly the post-partum period, likely confers the greatest risk of VTE, but the absolute risk is small given that the per-woman incidence and duration of pregnancy are low. Presently, guidelines for prevention of VTE during pregnancy are imprecise and are based on personal or family history of VTE or inherited thrombophilia, all of which often are unknown.

By contrast, menopause confers increased risk of atherosclerosis and other vascular events, such as venous thromboembolism, and the duration of exposure to the elevated risk lasts decades. The risk of acute myocardial infarction and other cardiovascular diseases rises sharply after menopause, but the risk can be reduced by managing risk factors (such as tobacco smoking, hypertension, hyperlipidemia, and overweight), through pharmacologic interventions (e.g., statins, anti-platelet compounds, oral anticoagulants, etc.), and surgical interventions (e.g., saphenous stripping, phlebectomy, or CHIVA procedures on varicose veins).

Annualized incidence of VTE varies significantly with ethnicity, overweight, hyperlipidemia, mobility, Vitamin D and general nutritional status, active malignancy, and other factors. For example, one study observed marked increases in risk of venous thromboembolism with decreasing tertiles of seasonally-adjusted plasma 25-hydroxy vitamin D concentrations. In the U.K., another study indicated postmenopausal incidence of VTE is approximately 6.7 per $10^4$ patient-years. In Taiwan, another study indicated the incidence is 4.4 vs. 2.6 per $10^4$ patient-years (adjusted hazard ratio 1.80, 95% confidence interval 1.27-2.54) in HRT users and nonusers, respectively. In the U.S., VTE incidence in Medicare-age women was 40.6 per $10^4$ person-years (PY), recurrence was 5.3/100 patient-years.

From these and other recent studies, it is estimated that VTE affects between 100,000 and 150,000 postmenopausal women each year in the U.S. In one study, 12-month post-VTE mortality was 22.5% from all causes, including 1.01% from pulmonary embolism, 10.4% from cancer, and 11.1% from other causes. Cancer-related VTE compared to non-cancer VTE had significantly (p<0.001) higher recurrence (9.9/100 patient-years vs. 4.4/100 patient-years) and mortality from all causes (45.9% vs. 12.3%).

The influence of HRT has been extensively studied in recent decades, and it is by now clear that HRT increases the risk of VTE. How much VTE risk is elevated depends on HRT type, oral vs. transdermal route of administration, chronicity of HRT use, age at onset of menopause, and other factors. The risk of VTE risk is higher in users of systemic combined estrogen-progestogen treatment than in users of estrogen only. Furthermore, the risk of VTE was lower for women who used local estrogen than among those using oral estrogen only. Transdermal estrogen only treatment and estrogen for local effect seem not to be related to an increased risk of VTE. Based on consistent biological and epidemiological findings, transdermal estrogen is the safest option with respect to VTE, especially in women at high risk. There is strong evidence that VTE risk is greater in women using medroxyprogesterone acetate compared with those receiving other progestins.

The use of HRT offers several benefits, in addition to mitigating symptoms of climacteric and other quality-of-life effects. For example, one meta-analysis showed that in eighteen trials (n=40,058) women using estrogen-only HRT compared with placebo had significantly lower risks, per 10,000 person-years, for diabetes (−19 cases [95% CI, −34 to −3]) and fractures (−53 cases [95% CI, −69 to −39]). Risks were significantly increased for venous thromboembolism (11 more cases per 10,000 person-years [95% CI, 3 to 22], and other conditions.

Women using estrogen-plus-progestin HRT compared with placebo experienced significantly lower risks, per 10,000 person-years, for colorectal cancer (−6 cases [95% CI, −9 to −1]), diabetes (−14 cases [95% CI, −24 to −3), and fractures (−44 cases [95% CI, −71 to −13). Risks were significantly increased for venous thromboembolism (21 more cases per 10,000 person-years [95% CI, 12 to 33]) and other conditions. Thus, decisions regarding use of HRT and prevention of VTE involve careful balancing of risks and benefits. For women who have high risk of osteoporosis progression but who also have contraindications to alternative prevention means, such as calcitonin, denosumab, raloxifene or tamoxifen, bazedoxifene, or bisphosphonates, HRT may be essential in preventing hip fractures.

For other women being treated for breast cancer, selective estrogen receptor modulators (SERMs) are compounds that act as estrogen agonists in some tissues and as estrogen antagonists in others. SERMs may be used to prevent breast cancer (tamoxifen, raloxifene), treat breast cancer (tamoxifen, toremifene), prevent and treat osteoporosis (raloxifene), and treat moderate to severe dyspareunia due to vaginal atrophy (ospemifene). Different SERMs provide different tissue-specific actions, allowing for individualization depending on the medical needs of postmenopausal women. Ordinarily, SERMS should not be used in women at high risk of venous thromboembolism because they substantially increase the risk of VTE events, including life-threatening pulmonary embolism. However, the potential benefits of SERM therapy may outweigh the potential risks of VTE provided that steps are taken to reduce VTE risk.

For such women and for others who have Factor V Leiden or other genetic mutations that markedly increase the risk of VTE, it would be desirable to be able to determine which women require intensive VTE prevention and, in those requiring such preventive interventions, which women may benefit from Factor Xa inhibitor, direct thrombin inhibitor, or complement C5a inhibitor therapy in addition to other modalities of prevention. Patients at risk of VTE, and particularly those having albumin level <2.0 gm/dL, customarily receive concomitant prophylactic dosing with low-molecular-weight heparin or low-dose warfarin. Patients with albumin levels of 2.0-3.0 gm/dL often receive aspirin, 75 mg once daily, or a P2Y12 inhibitor such as clopidogrel, 75 mg once daily. These traditional anticoagulants are not particularly effective in preventing VTE in menopause. Newer oral anticoagulants (e.g., dabigatran, rivaroxaban, apixaban, betrixaban, edoxaban, and otamixaban; approximately 6,000/yr AWP) may not be more effective in patients with menopause-related hypercoagulability insofar as they function at the same points in the coagulation cascade as traditional anticoagulants. However, eculizumab (Alexion Soliris®), a monoclonal antibody that is currently used in paroxysmal nocturnal hematuria (PNH), may be effective in preventing post-menopausal VTE whose origin includes complement activation. Eculizumab specifically binds to the complement protein C5 with high affinity, thereby inhibiting its cleavage to C5a and C5b and preventing the generation of the terminal complement complex C5b-9. Eculizumab inhibits terminal complement-mediated intravascular coagulation in menopausal patients and complement-mediated thrombotic microangiopathy (TMA). However, as described above, eculizumab is currently very expensive (400,000/yr AWP).

Accordingly, some embodiments described herein may be used for determining those circumstances where eculizumab may be needed. Embodiments of the technologies disclosed herein may be utilized for preventive, diagnostic, and treatment processes for venous thromboembolism in humans or other mammalian species. Additionally, some embodiments find notable applicability in the care of women after menopause, in whom high risk of VTE may be present and in whom conventional preventative methods, such as low-molecular-weight heparin, warfarin, or anti-platelet medications may not be efficacious. In such patients, use of other preventive methods, including direct oral anticoagulants and anti-complement medications such as eculizumab, may be clinically indicated. The latter, by binding to complement C5, prevents the formation of the MAC complex and activation of the downstream parts of the complement cascade, and thereby interdicts thromboembolism or other coagulopathy.

As described above, embodiments of the decision support tool described herein improve upon conventional sensors and technologies for detecting, ascertaining or treating the risk of VTE. In particular, the conventional technologies have a number of limitations and problems that are overcome by embodiments of the decision support tool or smart sensor described herein. For instance in contrast to embodiments of the technologies described herein, (1) conventional technologies for measurement physiological biomarkers for ascertaining VTE tend to be laborious, invasive, expensive, or not widely available. Additionally, (2) the biomarkers utilized by conventional technologies explain comparatively little of the variance in a population, such that statistical sensitivity and specificity when a conventional classifier or sensor apparatus is presented with new data are low, with many false-positive Type I errors and false-negative Type II errors.

Additionally, (3) these biomarkers are generally "lagging" indicators and denote the development of VTE and secondary processes in coagulation, inflammation, and endothelial injury that occur subsequent to VTE materializing. Such biomarkers are of greatest relevance in diagnosing VTE that has already occurred, whereas prevention of VTE depends upon identifying "leading" indicators, diagnostic changes in which arise well in advance of an acute and potentially life-threatening thromboembolic event.

Additionally, (4) for the conventional technologies, the turnaround times for performance of the assays are long, such that provisioning of the test results and predictions and classifications may be delayed by several days. In acute-care hospital settings, such delays are not commensurate with the within-day changes in the patient's condition and evolving risk for VTE, which is the subject of the preventive and therapeutic maneuvers.

Additionally, (5) an a priori unknown admixture of two or more phenotypic groups or genotypic pattern-based strata in a sampled population, particularly admixture of protective and risk rare variants, interferes with identification of groups (clusters), reduces statistical power, and increases the Type II false-negative error rate. That is, the conventional technologies are incompatible with the approaches undertaken by some of the embodiments of the improved decision support tool and smart sensor technology described herein.

These and other deficiencies and limitations of the conventional technologies are mitigated or overcome by the improved technologies described herein.

Figure 1A:
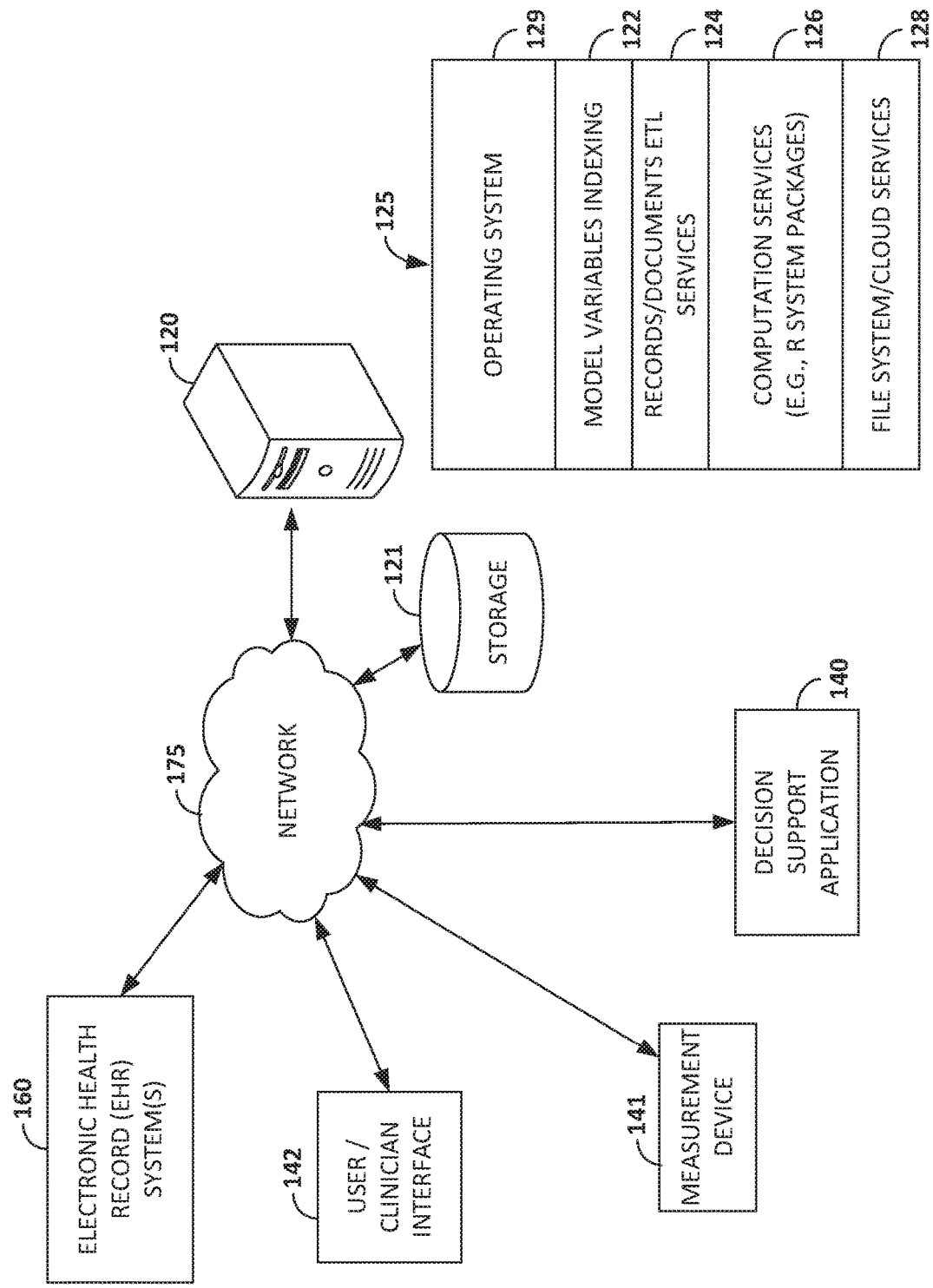
FIGS. 1A and 1B depict aspects of an illustrative operating environment suitable for practicing an embodiment of the disclosure.

Referring now to the drawings in general, and initially to FIG. 1A in particular, an aspect of an operating environment 100 is provided suitable for practicing an embodiment of the technologies described herein. We show certain items in block-diagram form more for being able to reference something consistent with the nature of a patent specification than to imply that a certain component is or is not part of a certain device. Similarly, although some items are depicted in the singular form, plural items are contemplated as well (e.g., what is shown as one data store might really be multiple data-stores distributed across multiple locations). But showing every variation of each item might obscure the invention. Thus for readability, we show and reference items in the singular (while fully contemplating, where applicable, the plural).

As shown in FIG. 1, a block diagram is provided showing aspects of an example computing system architecture suitable for implementing an embodiment of this disclosure and designated generally as example operating environment 100. Example operating environment 100 provides an aspect of a computerized system for compiling and/or running aspects of this disclosure including decision support tool and/or smart sensor apparatus, which may be incorporated into a decision support application. For example, in an embodiment, environment 100 may be used for monitoring, detecting or determining, and/or predicting a likely occurrence (or event) or future occurrence (or event) of VTE or another condition in a human patient, and additional decision support technology to facilitate caring for patients who may be prone to experience these conditions.

Operating environment 100 is one example of a suitable environment and system architecture for implementing an embodiment of the disclosure. Other arrangements and elements can be used in addition to or instead of those shown, and some elements may be omitted altogether for the sake of clarity. Further, as with operating environment 100, many of the elements described herein are functional entities that may be implemented as discrete or distributed components or in conjunction with other components, and in any suitable combination and location. As described above, some embodiments may be implemented as a system, comprising one or more computers and associated network and equipment, upon which a method or computer software application is executed. Accordingly, aspects of the present disclosure may take the form of an embodiment combining software and hardware aspects that may all generally be referred to herein as a "module" or "system." Further, the methods of the present disclosure may take the form of a computer application embodied in computer readable media having machine-readable application software embodied thereon. In this regard, a machine-readable storage media may be any tangible medium that can contain, or store a software application for use by the computing apparatus.

Computer application software for carrying out operations for system components or steps of the methods of the present disclosure may be authored in any combination of one or more programming languages, including an object-oriented programming language such as Java, Python, R, or C++ or the like. Alternatively, the application software may be authored in any or a combination of traditional non-object-oriented languages such as C or Fortran. The application may execute entirely on the user's computer (i.e., a computing device) as an independent software package, or partly on the user's computer in concert with other connected co-located computers or servers, or partly on the user's computer and partly on one or more remote computers, or entirely on a remote computer or collection of computers. In the latter cases, the remote computers may be connected to the user's computer through any type of network, including a local area network (LAN) or a wide area network (WAN), or the connection may be made to an external computer (for example, via the internet using an Internet Service Provider or ISP) or an arbitrary, geographically-distributed, federated system of computers, such as a cloud-based system.

Moreover, the components of operating environment 100, functions performed by these components, or services carried out by these components may be implemented at appropriate abstraction layer(s) such as the operating system layer, application layer, hardware layer, etc., of the computing system(s). Alternatively, or in addition, the functionality of these components and/or the embodiments described herein can be performed, at least in part, by one or more hardware logic components. For example, and without limitation, illustrative types of hardware logic components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc. Additionally, although functionality is described herein with regards to specific components shown in example operating environment 100, it is contemplated that in some embodiments functionality of these components can be shared or distributed across other components.

Environment 100 includes one or more electronic health record (EHR) systems, such as EHR system(s) 160 communicatively coupled to network 175, which is communicatively coupled to computer system 120. In some embodiments, components of environment 100 that are shown as distinct components may be embodied as part of or within other components of environment 100. For example, EHR system(s) 160 may comprise one or a plurality of EHR systems such as hospital EHR systems, health information exchange EHR systems, clinical genetics/genomics systems, ambulatory clinic EHR systems, psychiatry/neurology EHR systems, and insurance, collections or claims records systems; and may be implemented in or as a part of computer system 120. Similarly, EHR system(s) 160 may perform functions for two or more of types of EHR systems (not shown). EHR system(s) 160 also may include records of physiological variables (such as vital signs measurements) obtained via one or more measurement apparatus, tests, or screenings, such as measurement device 141.

In some embodiments of the technologies described herein, aspects of a decision support tool for patients having or at risk for developing a condition or event occurrence, such as VTE, or recurrence of a condition or event may utilize data about a population of patients derived from patient EHR or other records information. In particular, presently certain data warehouses are created for purposes of public health and observational research purposes as derived from electronic health records repositories in such a way that they are de-identified so as to comply with applicable confidentiality laws and regulations. The Cerner Health Facts™ data warehouse is such a system that has been curated for more than 15 years. It comprises a large 'transaction database' where each entry corresponds to a patient's 'basket' (a collection of items recorded or transacted at points in time during episodes of care services provisioning in the contributing health care institutions). Each database entry is ordered by the date-time of the transaction. Transaction sequencing is implemented by grouping medical events occurring in the same 'epoch' for the same patient together into 'baskets' and ordering the 'baskets' of each patient by the date-time stamps where the events occurred. Epoch durations may differ according to the age of the patient, or the acute or chronic nature of the health conditions that pertain to the patient, or the rate of change of the severity of the health conditions, or other factors, Epoch durations may be as short as a few minutes (as in critical care ICU or operating room contexts) or may be as long as 10 years or more (as in chronic ambulatory care-sensitive conditions, ACSCs).

Continuing with FIG. 1A, network 175 may comprise the Internet, and/or one or more public networks, private networks, other communications networks such as a cellular network, or similar network(s) for facilitating communication among devices connected through the network. In some embodiments, network 175 may be determined based on factors such as the source and destination of the information communicated over network 175, the path between the source and destination, or the nature of the information. For example, intra-organization or internal communication may use a private network or virtual private network (VPN). Moreover, in some embodiments items shown communicatively coupled to network 175 may be directly communicatively coupled to other items shown communicatively coupled to network 175.

In some embodiments, operating environment 100 may include a firewall (not shown) between a first component and network 175. In such embodiments, the firewall may reside on a second component located between the first component and network 175, such as on a server (not shown), or reside on another component within network 175, or may reside on or as part of the first component.

Embodiments of electronic health record (EHR) system(s) 160 include one or more data stores of health-related records, which may be stored on storage 121, and may further include one or more computers or servers that facilitate the storing and retrieval of the health records. In some embodiments, EHR system(s) 160 and/or other records systems may be implemented as a cloud-based platform or may be distributed across multiple physical locations. EHR system(s) 160 may further include record systems, which store real-time or near real-time patient (or user) information, such as wearable sensor or monitor, support-surface, bedside, laboratory, or in-home patient monitors or sensors, for example, such as measurement device 141.

Example operating environment 100 further includes a user/clinician interface 142 and decision support application 140, each communicatively coupled through network 175 to an EHR system 160. Although environment 100 depicts an indirect communicative coupling between interface 142 and application 140 with EHR system 160 through network 175, it is contemplated that an embodiment of interface 142 or application 140 are communicatively coupled to EHR system(s) 160 directly. For example, in one embodiment a decision support application 140 operating at least in part on a client device (such as a user-operated computer device like a tablet) includes an interface 142 (which may comprise a graphical user interface), which may be used for accessing patient information from an EHR system(s) 160.

An embodiment of decision support application 140 comprises a software application or set of applications (which may include programs, routines, functions, or computer-performed services) residing on a client computing device (or distributed in the cloud and on a client computing device) such as a personal computer, laptop, smartphone, tablet, or mobile computing device. In an embodiment, the application is a Web-based application or applet, and may be used to provide or manage user services provided by an embodiment of the technologies described herein, which may be used by a caregiver or screener to provide, for example, information about the likelihood of a specific patient or population of patients to have or develop a condition or health event, such as VTE, which may occur at a future time, and may further include a degree or level characterizing the severity of the condition or event. In some embodiments, application 140 includes or is incorporated into a smart sensor or computerized decision support tool, as described herein. Further, some embodiments of application 140 utilize user/clinician interface 142.

In some embodiments, application 140 and/or interface 142 facilitates accessing and receiving information from a user or health care provider about a specific patient or set of patients, according to the embodiments presented herein. Embodiments of application 140 also may facilitate accessing and receiving information from a user or health care provider about a specific patient, caregiver, or population including historical data; health care resource data; physiological variables or other patient-related measurements, time series, and predictions (including plotting or displaying the determined outcome and/or issuing an alert) described herein; or other health-related information, and facilitates the display of results, recommendations, or orders, for example. In an embodiment, application 140 also facilitates determining, receiving, or providing: notifications, recommendations, care plan changes, or orders, staffing scheduling, and/or queries from a user, which may be based on the results of monitoring and/or forecasted outputs, and which may in some embodiments utilize user interface 142. Decision-Support application 140 may also be used for providing diagnostic services or evaluation of the performance of various embodiments.

In some embodiments, user/clinician interface 142 may be used with application 140, such as described above. One embodiment of user/clinician interface 142 comprises a user interface that may be used to facilitate access by a user (including a clinician/caregiver such as a medical caregiver, physical therapist, or the like) to a probability, likelihood, forecast, score or prediction determined according to the technologies described herein, including information indicating a likelihood that a patient is experiencing a particular condition, such as VTE, or will experience (or is at risk for experiencing) such as condition or event, or other aspects described herein. One embodiment of interface 142 takes the form of a graphical user interface and application, which may be embodied as a software application (e.g., decision support application 140) operating on one or more mobile computing devices, tablets, smartphones, front-end terminals in communication with back-end computing systems, laptops, or other computing devices. In an embodiment, the application includes the PowerChart® software manufactured by Cerner Corporation. In an embodiment, interface 142 includes a Web-based application (which may take the form of an applet or app) or set of applications usable to manage user services provided by an embodiment of the technologies described herein.

In some embodiments, interface 142 may facilitate providing the output of the determined measurements, forecast(s), probabilities (or score), recommendations, scheduling orders, providing instructions (such as measuring, recording, and/or otherwise obtaining vital signs or other physiological variable measurements), confirmations or notifications (which may include, for example, confirmation that information has been received or notifications that information has not been received and there may be an error in the measuring instrument, user operation of a measurement device, or measurement procedure), reminders (such as notifications to obtain a physiological measurement sample), or outputs of other actions described herein, as well as logging and/or receiving other feedback from the user/caregiver, in some embodiments. In an embodiment, interface 142 also facilitates receiving orders for the patient from the clinician/user, based on the results of monitoring and predictions. Interface 142 also may be used for facilitating diagnostic services or evaluation of the performance of various embodiments.

Example operating environment 100 includes measurement device 141 communicatively coupled through network 175 to an EHR system 160. In an embodiment, measurement device 141 (sometimes referred to herein as an patient-interface component) comprises one or more sensor components operable to acquire clinical or physiological information about a patient, such as various types of physiological measurements, physiological variables, or similar clinical information associated with a particular physical or mental state of the patient, which may comprise input data into a classifier component of a decision support tool, and which may be acquired periodically, continuously, as needed, or as they become available, and may be represented as one or more time series of measured variables. In one embodiment, measurement device 141 comprises sensors for obtaining (and in some instances pre-processing or interpreting) non-invasive recording of vital signs or other physiological or patient-related data, which may be obtained continuously, periodically, or at irregular intervals. Accordingly, the term measurement is used broadly herein, and it is contemplated that in some embodiments, measurement device 141 may not perform measurement but may receive information about physiological parameters (such as genotypic or phenotypic information, other measurements such as heart rate (HR), blood pressure (e.g., systolic blood pressure or SBP), respiratory rate (RR), for example and without limitation) which may be measured, observed, or otherwise recorded. Some embodiments of measurement device 141 may comprise one or more sensors, an interface component, and/or processing/communications component (not shown).

In some embodiments, measurement device 141 may include a Bluetooth or wireless communication data-transfer capability and may be wirelessly communicatively coupled with an application on a computing device, such as a smartphone an app or aspect of decision support application 140. In some embodiments, measurement device 141 comprises patient bedside monitor, such used in hospital. In an embodiment, one or more sensor components of measurement device 141 may comprise a user-wearable sensor component or sensor component integrated into the patient's environment. Examples of sensor components of measurement device 141 include a sensor positioned on an appendage (on or near the user's head, attached to the user's clothing, worn around the user's head, neck, leg, arm, wrist, ankle, finger, etc.); skin-patch sensor; ingestible or subdermal sensor; sensor component(s) integrated into the user's living environment (including the bed, pillow, or bathroom); and sensors operable with or through a smartphone carried by the user, for example. It is also contemplated that the clinical or physiological information about patient, such as the monitored variables and/or clinical narratives regarding the patient, used according to the embodiment of the invention disclosed herein may be received from human measurements, human observations, or automatically determined by sensors in proximity to the patient. For example, in one embodiment, a nurse periodically measures a patients' blood pressure and enters the measurement and/or observations via user/clinician interface 142. In another example, a nurse or caregiver enters one or more progress notes for an in-patient via user/clinician interface 142. Similarly, values for other physiological variables or patient data may be entered via user/clinician interface 142.

Examples of physiological variables monitored by measurement device 141 can include vital signs variables, such as heart rate (bradycardia and tachycardia) and blood pressure (hypotension and hypertension), oxygen saturation (peripheral desaturation), other vital signs, or physiologic or patient as described herein, such as complement protein values (e.g., such as one or more of C1 through C9, or "total complement" CH50). In some embodiments, complement proteins C3, C4, and C50 are received by measuring device 141, and may be received or determined from lab results for the patient. In some embodiments physiological variables monitored by measurement device 141 may include any type of measureable, determinable, or observable physiological or clinical variable or characteristic associated with a patient, which in some embodiments may be used for forecasting a future value (of the measured variable, a composite variable based on one or more measured variables, or other factor determined at least in part from one or more measured variables) of a patient in order to facilitate clinical decision making. In an embodiment, a measurement device 141 comprises a sensor probe and a communication link that periodically transmits identification information and probe data to a decision support application 140, so that a time series of monitored values is stored in a record associated with the patient on an EHR system 160, thereby enabling the decision support application 140 to form a raw binary alarm indication and/or a physiological variable decision statistic.

Embodiments of measurement device 141 may store user-derived data locally or communicate data over network 175 to be stored remotely. Some embodiments of measurement device 141 include a monitor interface, which may be embodied as I/O such as buttons and sounds emitted from the measurement device 141, its firmware or software application or app operating on a user's mobile device or computer system 120, and in an embodiment may facilitate uploading of measured (or recorded, or otherwise received) information from measurement device 141 to computer system 120. Additionally, some embodiments of measurement device 141 include functionality for processing user-derived information locally or for communicating the information to computer system 120, where it is processed. In some embodiments, the processing may be carried out or facilitated by one or more software agents, as described below. In some embodiments the processing functionality, performed on measurement device 141 and/or computer system 120 includes pre-processing and/or signal conditioning, such as removing noise or erroneous information.

Example operating environment 100 further includes computer system 120, which may take the form of one or more servers, and which is communicatively coupled through network 175 to EHR system 160, and storage 121.

Computer system 120 comprises one or more processors operable to receive instructions and process them accordingly, and may be embodied as a single computing device or multiple computing devices communicatively coupled to each other. In one embodiment, processing actions performed by system 120 are distributed among multiple locations such as one or more local clients and one or more remote servers, and may be distributed across the other components of example operating environment 100. For example, aspects of application 140 or interface 142 may operate on or utilize computer system 120. Similarly, a portion of computing system 120 may be embodied on user interface 142, application 140, and/or EHR system(s) 160. In one embodiment, system 120 comprises one or more computing devices, such as a server, desktop computer, laptop, or tablet, cloud-computing device or distributed computing architecture, a portable computing device such as a laptop, tablet, ultra-mobile P.C., or a mobile phone.

Embodiments of computer system 120 include computer software stack 125, which in some embodiments operates in the cloud, as a distributed system on a virtualization layer within computer system 120, and includes operating system 129. Operating system 129 may be implemented as a platform in the cloud, and which is capable of hosting a number of services such as 122, 124, 126, and 128. Some embodiments of operating system 129 comprise a distributed adaptive agent operating system. Embodiments of services 122, 124, 126, and 128 run as local services or may be distributed across one or more components of operating environment 100, in the cloud, on one or more personal computers or servers such as system 120, and/or a computing device running interface 142 or application 140. In some embodiments, interface 142 and/or application 140 operate in conjunction with software stack 125.

In embodiments, model variables indexing (or mapping) service 122 and records/documents ETL service 124 provide services that facilitate retrieving patient variables such as physiological or other measurements, which may include frequent item sets, extracting database records, and/or cleaning the values of variables in records. For example, services 122 or 124 may perform functions for synonymic discovery, indexing or mapping variables in records, or mapping disparate health systems' ontologies, such as determining that a particular medication frequency of a first record system is the same as another record system. Some embodiments of stack 125 may also include predictive models service (not show), which in general is responsible for providing models such as multi-variable models, for detecting or predicting a particular condition or event utilizing a classifier apparatus, such as described herein. In some embodiments, services 122 and/or 124 may invoke computation services 126.

Computation services 126 may perform statistical software operations, and may include statistical calculation packages such as, in one embodiment, the R system (the R-project for Statistical Computing, which supports R-packages or modules tailored for specific statistical operations, and which is accessible through the Comprehensive R Archive Network (CRAN) at http://cran.r-project.org) or similar services. In an embodiment, computation services 126 and include computer-performed services or routines, which may be embodied as one or more software agents or computer program routines such as the example embodiments of computer program routines illustratively provided in FIGS. 11A-11E. In one embodiment, computation services 126 comprises the R-System DirichletReg package, for determining Dirichlet regression models. Additional details about example computation services 126 are provided in the example computer program routines of FIGS. 11A-11E, and described further in connection to FIG. 2.

Computation services 126 also may include natural language processing services (not shown) such as Discern nCode™ developed by Cerner Corporation, or similar services. In an embodiment, computation services 126 include the services or routines, which may be embodied as one or more software agents or computer software routines such as the example embodiments of computer program routines illustratively provided in FIGS. 11A-11E. Computation services 126 also may include services or routines for utilizing one or more classification models or processes, such as described in connection to FIG. 2 and the example computer program routines illustratively provided in FIGS. 11A-11E. In some embodiments, computation services 126 use EHR system(s) 160, model data and model storage services (not shown), and/or other components of example operating environment 100, and may also include services to facilitate receiving and/or pre-processing physiological (or other patient-related) data. For instance, model data and model storage services may be utilized to perform services for facilitating storage, retrieval, and implementation of the forecasting models described herein and of the data used in models, classifier apparatus, or predictive services.

In some embodiments, stack 125 includes file system or cloud-services 128. Some embodiments of component 128 may comprise an Apache Hadoop and Hbase framework, or similar frameworks operable for providing a distributed file system, and which in some embodiments facilitate provide access to cloud-based services, such as those provided by Cerner Healthe Intent®. Additionally or alternatively, some embodiments of file system or cloud-services 128 or embodiments of stack 125 may comprise one or more stream processing service(s). For example, such stream processing service(s) may be embodied using IBM InfoSphere stream processing platform, Twitter Storm stream processing, Ptolemy or Kepler stream processing software, or similar complex event processing (CEP) platforms, frameworks, or services, which may include the user of multiple such stream processing services (in parallel, serially, or operating independently). Some embodiments of the invention also may be used in conjunction with Cerner Millennium®, Cerner CareAware® (including CareAware iBus®), Cerner CareCompass®, or similar products and services.

Example operating environment 100 also includes storage 121 (or data store 121), which in some embodiments includes patient data for a candidate or target patient (or information for multiple patients), including raw and processed patient data; variables associated with patient diagnoses or determinations, recommendations; recommendation knowledge base; recommendation rules; recommendations; recommendation update statistics; an operational data store, which stores events, frequent item sets (such as "X often happens with Y", for example), and item sets index information; association rule-bases; agent libraries, solvers and solver libraries, and other similar information including data and computer-usable instructions; patient-derived data; and health care provider information, for example. It is contemplated that the term data includes any information that can be stored in a computer-storage device or system, such as user-derived data, computer usable instructions, software applications, or other information. In some embodiments, data store 121 comprises the data store(s) associated with EHR system 160. Further, although depicted as a single storage data store, data store 121 may comprise one or more data stores, or may be in the cloud.

Figure 1B:
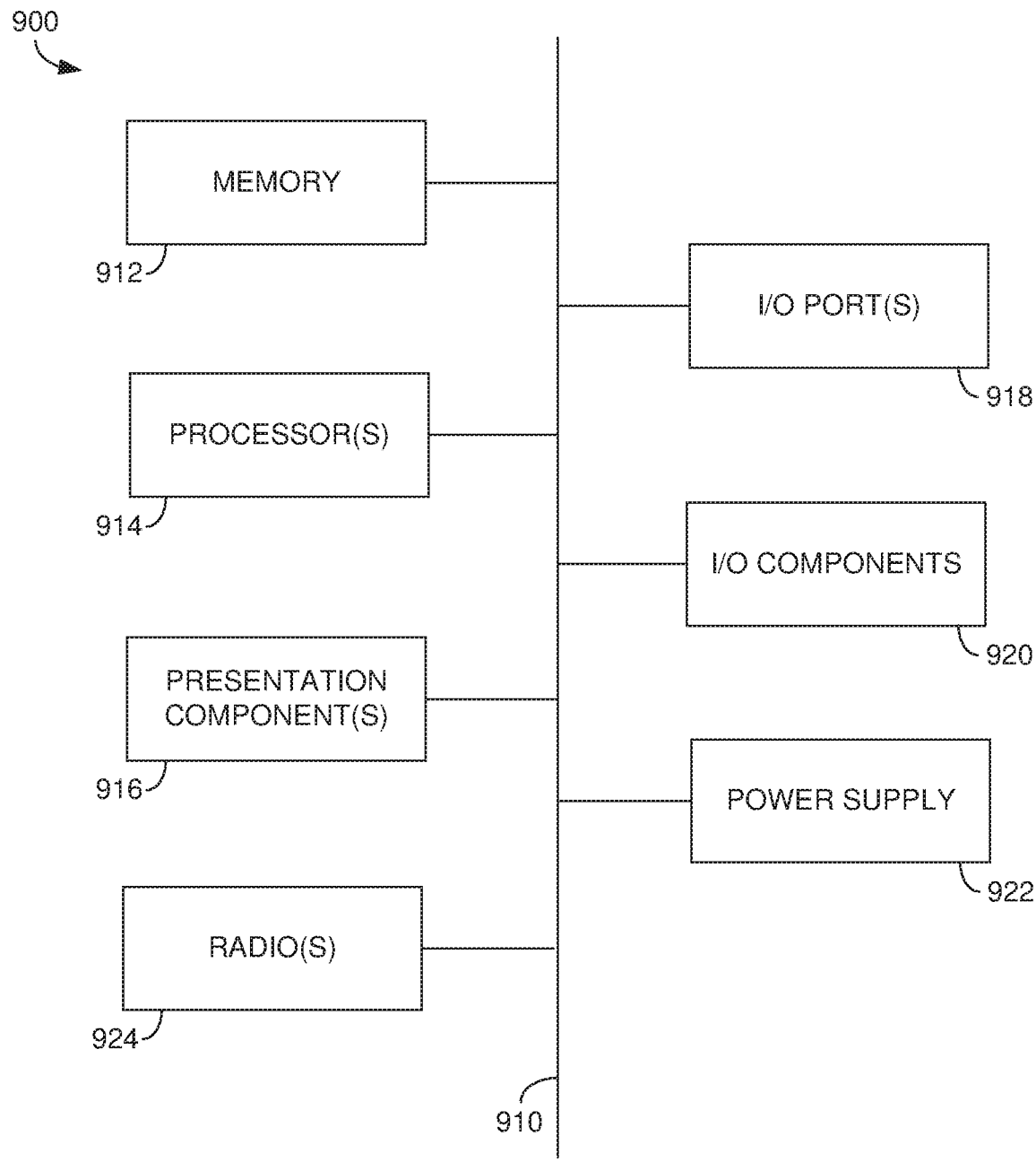

Turning briefly to FIG. 1B, there is shown one example embodiment of computing system 900 representative of a system architecture that is suitable for computer systems such as computer system 120. Computing device 900 includes a bus 910 that directly or indirectly couples the following devices: memory 912, one or more processors 914, one or more presentation components 916, input/output (I/O) ports 918, input/output components 920, radio 924, and an illustrative power supply 922. Bus 910 represents what may be one or more busses (such as an address bus, data bus, or combination thereof). Although the various blocks of FIG. 1B are shown with lines for the sake of clarity, in reality, delineating various components is not so clear, and metaphorically, the lines would more accurately be grey and fuzzy. For example, one may consider a presentation component, such as a display device, to be an I/O component. Also, processors have memory. As such, the diagram of FIG. 1B is merely illustrative of an example computing system architectures that can be used in connection with one or more embodiments of the present disclosure. Distinction is not made between such categories as "workstation," "server," "laptop," "hand-held device," etc., as all are contemplated within the scope of FIG. 1B and reference to "computing system."

Computing system 900 typically includes a variety of computer-readable media. Computer-readable media can be any available media that can be accessed by computing system 900 and includes both volatile and nonvolatile media, and removable and non-removable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing system 900. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above may be included within the scope of computer-readable media.

Memory 912 includes computer-storage media in the form of volatile and/or nonvolatile memory. The memory may be removable, non-removable, or a combination thereof. Exemplary hardware devices include solid-state memory, hard drives, optical-disc drives, etc. Computing system 900 includes one or more processors that read data from various entities such as memory 912 or I/O components 920. In an embodiment, storage 121 is embodied as memory 912. Presentation component(s) 916 present data indications to a user or other device. Exemplary presentation components include a display device, speaker, printing component, vibrating component, etc. In an embodiment, functionality provided via user/clinician interface 142 is facilitated by one or more presentation components 916.

In some embodiments, computing system 924 comprises radio(s) 924 that facilitates communication with a wireless-telecommunications network. Illustrative wireless telecommunications technologies include CDMA, GPRS, TDMA, GSM, LTE, WiMAX, and the like. Radio 924 may additionally or alternatively facilitate other types of wireless communications including Wi-Fi, Bluetooth, NFC, other types of RF communication, light, infrared, or the like. As can be appreciated, in various embodiments, radio 924 can be configured to support multiple technologies and/or multiple radios can be utilized to support multiple technologies.

I/O ports 918 allow computing system 900 to be logically coupled to other devices, including I/O components 920, some of which may be built in. Illustrative components include a microphone, joystick, game pad, satellite dish, scanner, printer, wireless device, etc. The I/O components 920 may provide a natural user interface (NUI) that processes air gestures, voice, or other physiological inputs generated by a user. In some instances, inputs may be transmitted to an appropriate network element for further processing. An NUI may implement any combination of speech recognition, stylus recognition, facial recognition, biometric recognition, gesture recognition both on screen and adjacent to the screen, air gestures, head and eye tracking, and touch recognition (as described in more detail below) associated with a display of the computing system 900. The computing system 900 may be equipped with depth cameras, such as stereoscopic camera systems, infrared camera systems, RGB camera systems, touchscreen technology, and combinations of these, for gesture detection and recognition. Additionally, the computing system 900 may be equipped with accelerometers or gyroscopes that enable detection of motion.

The architecture depicted in FIG. 1B is provided as one example of any number of suitable computer architectures, such as computing architectures that support local, distributed, or cloud-based software platforms, and are suitable for supporting computer system 120.

Returning to FIG. 1A, in some embodiments, computer system 120 is a computing system made up of one or more computing devices. In some embodiments, computer system 120 includes one or more software agents, and in an embodiment includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system.

Figure 2:
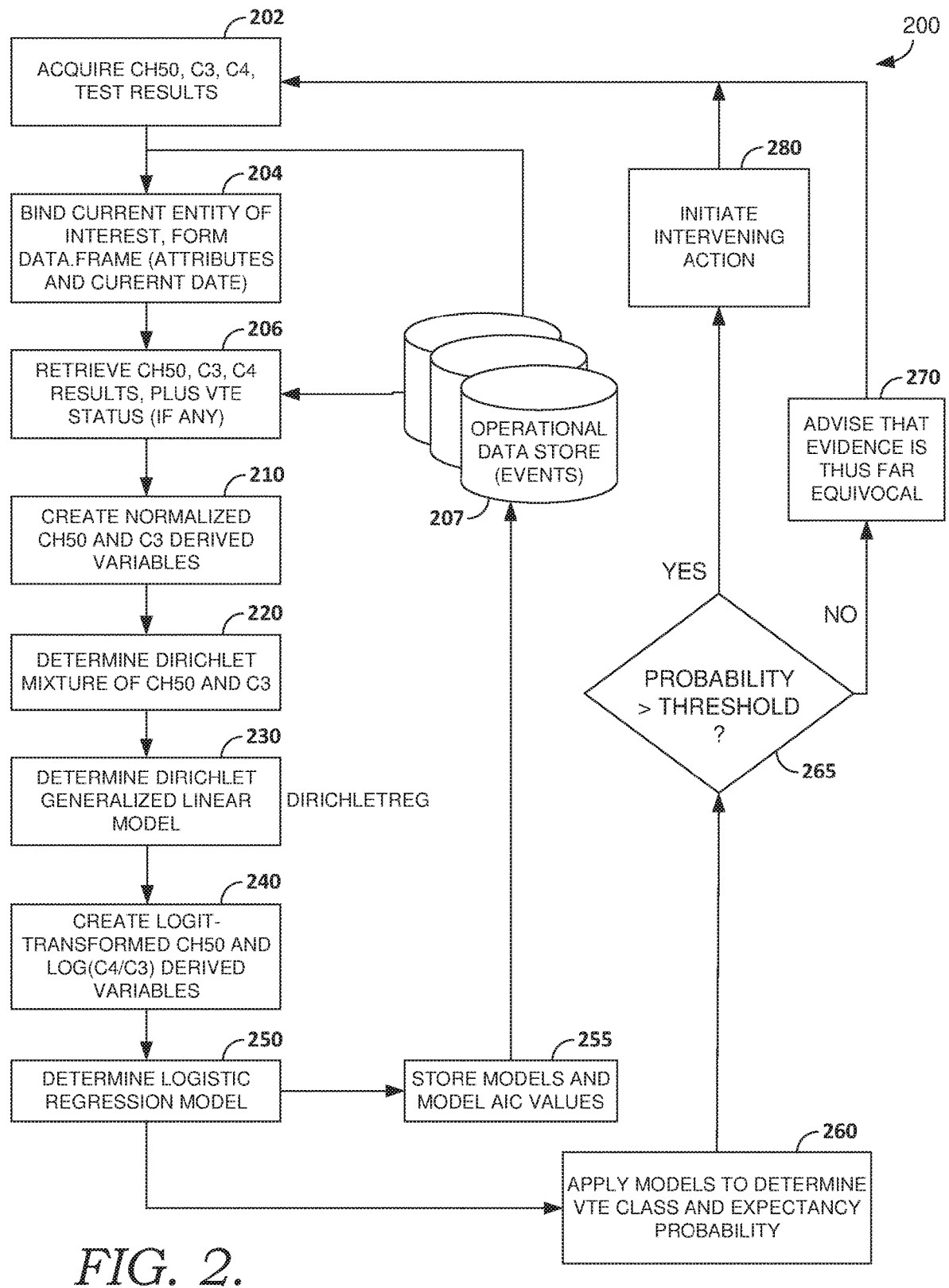
FIG. 2 depicts a flow diagram of a method for conditionally initiating an intervening action based on determining a patient is at risk for VTE, in accordance with an embodiment of the disclosure.

Turning now to FIG. 2, one example embodiment is provided of a method 200 for conditionally initiating an inventing action based on a patient's risk of VTE. In particular, method 200 generates and utilizes an embodiment of an improved smart sensor for detecting and ascertaining the patient's risk of VTE. In one embodiment, the smart sensor comprises a computer-implemented sensor or software-based computerized sensor that utilizes the newly discovered aspects of physiological data of a patient described herein, and employs a novel process to derive new information from the aspects of physiological data, and then applies a machine-learning classifier/predictor to ultimately detect risk for emergence of VTE in the patient. According to embodiments described in connection to FIG. 2, a quasi-Dirichlet distribution "mixture" relationship between total hemolytic complement (CH50) activity and complement protein C3 levels is employed as part of the smart sensor. In particular, method 200 includes determining Dirichlet regression and logistic regression models for VTE prediction and risk classification.

The Dirichlet process is a stochastic process used in Bayesian nonparametric models of data, particularly in Dirichlet process mixture models (also known as infinite mixture models). It is a distribution over distributions; that is, each draw from a Dirichlet process is itself a distribution. It is called a Dirichlet process because it has Dirichlet-distributed finite-dimensional marginal distributions, in a manner analogous to the Gaussian process, another popular stochastic process used for Bayesian nonparametric regression, which has Gaussian-distributed finite-dimensional marginal distributions. A Dirichlet process is a process whose sample paths are probability measures with probability equal to one. As noted above, a normalization check or transformation procedure may be employed, to insure that the plurality of variables contributing to the mixture does sum to one.

Accordingly, method 200 begins at step 202, wherein CH50, C3, and C4 information about a human patient are received. The CH50, C3, and C4 information may be received form laboratory test results for a patient, from a patient's health record (such as EHR system 160), and/or from a measurement device. In some embodiments, step 202 may receive this information using measurement device 141 (FIG. 1A). In some embodiments of step 202, a collection of controls and cases are acquired whose VTE classifications are known and whose relevant complement CH50, C3, and C4 covariables' values are also known. Some embodiments of method 200 may further include, at step 204, associating a particular patient with the measurement device 141, and/or binding information about the patient or patient's EHR and initializing a data.frame (e.g., attributes and current date) for acquiring the CH50, C3, and C4 information. Additionally, some embodiments, at step 206, receive CH50, C3, and C4 results, plus VTE status for a patient, if any such data is available.

At step 210, create normalized CH50 and C3 derived variables. In some embodiments, the range of the derived variables are normalized so that their sum is equal to one. At step 220, determine Dirichlet mixture of ch50 and c3. In some embodiments of step 210 and 220, the values of the CH50 and C3 complement proteins are transformed as a quasi-Dirichlet mixture, normalizing the range of the derived variables that their sum is equal to one.

At step 230 determine a Dirichlet generalized linear model. Some embodiments of step 230 comprise determining a "null model." In some embodiments, the null model may be determined by logistic regression Dirichlet regression, support vector machine, neural network, random forest, gradient boosting, or other suitable means, to establish the statistical relation of the covariables to the VTE classifications. The resulting null model and metadata may be stored computer memory, such as operational data store 207, which may be embodied as storage 121, for subsequent use. In particular, in some embodiments, the null model may be utilized as an input to determine the statistical significance of relations of the plurality of quasi-Dirichlet derived variables to the VTE classification by a method such as the Dirichlet regression or a finite mixture regression model. Some embodiments of steps 210, 220, and 230 may be carried out using the example computer program routine illustratively shown FIGS. 11A-11E.

At step 240, create logit-transformed CH50 and log(C4/C3) derived variables. Embodiments of step 240 determine a log-transform of the raw CH50 values to create an ancillary derived variable, and a log-transform of the ration of C4 to C3 to also create an ancillary derived variable.

At step 250, determine a logistic regression model for the classification/prediction of VTE. Embodiments of step 250 determine a classification/prediction model using the derived variables to estimate the likelihood of venous thromboembolic event(s). In some embodiments, the Akaike information criterion (AIC), an estimator of the relative quality of the model, may be determined. At step 255, store the models and model AIC values. Embodiments of step 255 store the models and AIV values for subsequent use.

At step 260, apply the models to determine VTE class and expectancy probability for a new case. In embodiments of step 260, CH50, C3, and C4 data may be received for a new case, corresponding to a new patients whose likelihood of VTE event(s) is to be determined. The new case's data may be transformed to the derived Dirichlet-transformed, logit-transformed, and log-transformed forms determined in steps 210 and 240. Then the model determined in step 250 may be applied to the new case's transformed data so to determine estimated classification/prediction of VTE event(s) likelihood.

At step 265, the expectancy probability may be evaluated against a threshold. The threshold may be pre-determined, determined by a clinician, or determined based on the particular condition of the patient. In an embodiment, a threshold of fifty percent is utilized. In another embodiment, a threshold corresponding to the patient's risk for developing VTE is utilized and may be as low as ten to twenty percent for indicating the patient has a moderate to moderately high risk for developing VTE.

Where the threshold is not satisfied, then it may be determined that the patient does not have a sufficient risk for VTE. In an embodiment, at step 270, a decision support tool may advice that results do not indicate a risk for VTE. In some embodiments, method 200 may be reapplied for other patients as needed, and/or method 200 may return to step 202 wherein a new classification model for the smart sensor or decision support tool, may be determined and then subsequently utilized for a patient.

Where the threshold is satisfied, in step 265, and thus the expectancy probability, which may correspond to the patient's risk for VTE, is high or at least above the threshold, then at step 280 a decision support tool running method 200 may initiate an intervening action. For instance, a notification may be provided to a caregiver that the patient is at risk for VTE, and/or another intervening action may be invoked or otherwise carried out. For instance, one intervening action comprises generating a notification that may be emitted or otherwise communicated to the patient or to a caregiver, such as a provider clinician responsible for the care of the patient. For example, an electronic advisory or warning message may be emitted to a human user, such as a caregiver, indicating an elevated risk of VTE for the patient. In an embodiment, the action comprises generating and emitting or communicating the notification, which may be emitted/communicated via a bedside or patient-side alarm, user/clinician interface (such as interface 142 described in FIG. 1A), or may be communicated to a smartphone or personal computing device of a caregiver, thereby alerting them of an impending deterioration of the patient's condition. In one embodiment, the notification comprises an event signal and includes the likelihood of future VTE.

Another intervening action that may be initiated, based on the determined likelihood, comprises modifying a care plan or treatment procedure or a recommendation for modifying a care plan or treatment procedure associated with the patient; for example, automatically scheduling an appointment with a specialist or other healthcare resources for the patient, operating on the patient, or administering another similarly effective therapeutic intervention. The recommendation may be provided in conjunction with a notification, and/or may be provided via a user/clinician interface, such as interface 142, described in connection with FIG. 1A.

Yet another action that may be initiated, based on the determined likelihood, comprises automatically modifying computer code executed in a healthcare software program for treating the patient, thereby transforming the program at runtime. For example in one embodiment, the modification comprises modifying (or generating new) computer instructions to be executed at runtime in the program, the modification may correspond to a change in a care plan, treatment procedure, or therapeutic intervention to be administered to the patient due to the determined likelihood of VTE occurrence. In one instance, the modification comprises changing the executed computer instructions corresponding to monitoring the patient's condition, such as increasing the frequency of obtaining physiological measurements of the patient, or increasing sensitivity of monitoring physiological changes in a patient.

Yet another action that may be initiated, based on the determined likelihood, comprises scheduling healthcare resources for the patient. For example in one embodiment, a physical therapy resource may be automatically reserved for the patient, healthcare staff may be notified and/or automatically scheduled, or transportation/support staff or resources for getting the patient to a healthcare facility may be called. In one embodiment, this action comprises modifying or updating a resource/scheduling electronic record in a resource/scheduling system, such as operated as part of a hospital or healthcare system. In one embodiment, the action comprises, upon a determined likelihood of a VTE event occurrence, initiating a computer instruction that modifies the scheduling healthcare resources, which may include computer instructions for automatically alerting, scheduling, and/or notifying staff, reserving rooms, transportation, or other equipment/space, and which may include changing the priority of the patient (when compared to other patients) for receiving these resources.

In some embodiments of method 200, the statistical performance quality of the classification model, determined in step 250, may be determined. For example in an embodiment, the statistical performance may be determined in terms of sensitivity, specificity, total error rate, or other criteria as are known in the art. The statistical performance of an embodiment actually reduced to practice is shown in FIG. 10. The determined and validated model then may be implemented within a smart sensor and/or as part of a decision support tool. In some embodiments of method 200, fractional logit methods may be substituted for the Dirichlet regression modeling method of step 230. In yet other embodiments, multivariate normal models for logit-transformed dependent variables may be utilized, as another alternative.

Example Reduction to Practice

An illustrative example embodiment of the present disclosure that was actually reduced to practice is now described. In this example, a decision support tool comprising an embodiment of the improved smart sensor was utilized to determine patients at risk for VTE. In particular, this example embodiment determines a classification of the risk of venous thromboembolism in postmenopausal women. Other embodiments may create a classification/prediction system whose model means are calibrated for men. Yet other embodiments may have models directed to estimating VTE risk in men and women of younger ages or in children.

With reference to FIGS. 9A, 9B, 10 and with continuing reference to method 200 of FIG. 2 the example embodiment actually reduced to practice is now described. The records of 89 postmenopausal women experiencing venous thromboembolic events (VTE, as determined by clinical exam) during medical or surgical admissions to 451 U.S. acute-care hospitals between 1 Jan. 2010 and 31 Dec. 2016 were retrieved and screened, as were the records of 411 postmenopausal women admitted to the same institutions during the same time period who did not experience VTE. These records were retrieved from Cerner Health Facts® data warehouse, an electronic health record (EHR system 160) derived, HIPAA-compliant de-identified repository containing the longitudinally-linked health records of more than 100 million persons receiving care at 824 U.S. based institutions. Results for CH50 (LOINC 4532-8; CPT-4 86162), C3 (LOINC 4485-9; CPT-4 86160), and C4 (LOINC 4498-2; CPT-4 86160) were retrieved for the 411 postmenopausal women without VTE and for the 89 postmenopausal women diagnosed with VTE. In addition to age >45 years, the cohort studied was required to have menopause denoted by ICD code (ICD-9 627.xx or ICD-10 N95). Ascertainment of VTE diagnosis was also made on the basis of ICD codes (ICD-9 453.xx, V12.51; ICD-10 I80.xx, I82.xx; Z86.71x, Z86.72x). Women whose records were included in the building and validation of the system and method ranged in age from 45 to 87.

In this example embodiment, a computer system 120 running the Linux operating system (129) was utilized with the open-source software package R, and the R packages (computation services 126): DirichletReg, for determining a Dirichlet regression model. This example embodiment also used the example computer program routine provided in FIGS. 11A-11E.

Logistic regression was performed with the VTE dependent variable regressed on the Dirichlet-transformed CH50-C3 variables pair, on the logit-transformed CH50 variable, and on the log-transformed ratio of C4 to C3.

With reference to FIGS. 9A and 9B, example graphical user interfaces 900 and 901 are provided for a decision support tool embodiment showing a patient determined to have a low risk (5%) and moderately high risk (25%) for VTE, respectively. In an embodiment, graphical user interfaces 900 and 901 may be embodied as user/clinician interface 142, described in FIG. 1A. In these example user interfaces, it can be seen that the embodiment of the decision support tool relies on C3, C4, and CH50 values from the patient, which may be received from measurement device 141. FIGS. 9A and 9B also depict classification model parameters 950, which may be determined according to steps 202 through 255 of method 200, in an embodiment. In one embodiment, a percent likelihood may be determined using the model parameters 950, as percent likelihood=EXP (6.98+−7.6*X1+12.18*X2)/(1+EXP(6.98+−7.6*X1+12.18*X2)); wherein X1=EXP(−4.81+0.043*CH50)/(1+EXP(−4.81+0.043*CH50)), and X2=LOG 10(C4/C3).

In the example embodiment actually reduced to practice, the resulting model had an accuracy of 95%, with sensitivity 87% and specificity 98%, as shown in FIG. 10, and thus represents a significant improvement over the conventional VTE-detection technologies. In particular, embodiments of the example decision support tool for determining risk of VTE utilizing the improved smart sensor or decision support tool described herein may result in the saving of many additional patient lives.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

As used herein and in connection with the clauses listed hereinafter, the terminology "any of clauses" or similar variations of said terminology is intended to be interpreted such that features of claims/clauses may be combined in any combination. For example, an exemplary clause 4 may indicate the method/apparatus of any of clauses 1 through 3, which is intended to be interpreted such that features of clause 1 and clause 4 may be combined, elements of clause 2 and clause 4 may be combined, elements of clause 3 and 4 may be combined, elements of clauses 1, 2, and 4 may be combined, elements of clauses 2, 3, and 4 may be combined, elements of clauses 1, 2, 3, and 4 may be combined, and/or other variations. Further, the terminology "any of clauses" or similar variations of said terminology is intended to include "any one of clauses" or other variations of such terminology, as indicated by some of the examples provided above.

Clause 1. A computer system for detecting and treating venous thrombosis and venous thromboembolism (VTE) in a human patient: a processor; computer memory having instructions stored thereon that when executed by the processor perform operations comprising: receiving compliment protein levels for a patient including CH50, C3, and C4 levels; determining a Dirichlet mixture of CH50 and C3, normalizing the CH50 and C3 derived variables; create logit-transformed CH50 and Log(C4/C3) derived variables; utilizing a logistic regression classification model, apply the classification model to the transformed and derived variables to determine a VTE class and expectancy probability for the patient; based on a comparison of the determined expectancy probability and a threshold, determine that the patient is at risk for VTE when the threshold is satisfied; and initiating an intervening action for the human patient.

Clause 2. The computer system of clause 1, the logistic regression classification model is determined by: receiving CH50, C4, and C3 information for a population of patients representing a baseline; determining a Dirichlet mixture of CH50 and C3, normalizing the CH50 and C3 derived variables; determining a Dirichlet generalized linear model; creating logit-transformed CH50 and Log(C4/C3) derived variables; utilizing the generalized linear model and the transformed variables, determine a logistic regression classification model; and storing the determined classification model in computer memory thereby enabling the model to be utilized by a smart sensor or decision support tool.

Clause 3. The computer system of clause 1 or 2, wherein the intervening action comprises at least one of: issuing a notification to a caregiver associated with the patient; automatically scheduling healthcare resources for treating the patient; or modifying a computer program associated with a care plan for the patient.

Clause 4. A computer readable media comprising computer-executable instructions that when executed by a processor cause the processor to implement a computer software application that provides a clinical decision support tool for diagnosing venous thromboembolism (VTE), the instructions comprising: receiving a data set having a plurality of types of biomarkers which are interrelated to each other and to phenotypic VTE status and risk of developing one or more VTE events; determining a null classification/prediction model for VTE as a function the biomarkers; using said null model to adjust for quasi-Dirichlet distributions of the biomarkers' values, determining whether statistically significant relationship(s) exist associating the biomarkers to phenotypic VTE status and risk; transforming the biomarkers' values as a quasi-Dirichlet mixture, normalizing the range of the derived variables so as to insure that their sum always is equal to 1; and logit-transforming one of the biomarkers; log-transforming a ratio of two other biomarkers; and determining a classification/prediction model for the VTE dependent variable as a function of the biomarkers' transformed values.

Clause 5. The computer readable media of clause 4 further comprising: receiving new data sets whose biomarker values; transforming the new biomarkers' values as a quasi-Dirichlet mixture, normalizing the range of the derived variables so as to insure that their sum always is equal to 1; applying the classification/prediction model to determine a resulting state vector $\{y_k\}$; based on the resulting state vector, determining that the patient has a risk for VTS; and initiating an intervening action.

Clause 6. The computer readable media of clauses 4 or 5, wherein the intervening action comprises at least one of: issuing a notification to a caregiver associated with the patient; automatically scheduling healthcare resources for treating the patient; or modifying a computer program associated with a care plan for the patient.

Clause 7. The computer readable media of any of clauses 4 through 6, wherein the biomarkers data set comprises quantitative CH50, C3, and C4 measurements of serum from the patient.

Clause 8. The computer readable media of any of clauses 4 through 7, wherein the null model is determined by logistic regression, Dirichlet regression, support vector machine, neural network, random forest, gradient boosting, or other means as are known in the art, establishing the statistical relation of the covariables to the VTE classifications.

Clause 9. The computer readable media of any of clauses 4 through 8, wherein the null model is used as an input to determine the statistical significance of relations of the plurality of quasi-Dirichlet derived variables to the VTE classification by a method such as a Dirichlet regression or a finite mixture regression model.

Clause 10. The computer readable media of any of clauses 4 through 9, wherein logit-transformation of the raw CH50 values is performed to create an ancillary derived variable.

Clause 11. The computer readable media of any of clauses 4 through 10, wherein log-transformation of the ratio of C4 to C3 is performed to create an ancillary derived variable.

Clause 12. The computer readable media of any of clauses 4 through 11, wherein a classification/prediction model is determined using said derived variables to estimate the likelihood of venous thromboembolic event(s), by logistic regression, support vector machine, gradient boosting, random forest, neural network.

Clause 13. The computer readable media of any of clauses 4 through 12, wherein the statistical performance quality of the classification/prediction model is determined in terms of sensitivity, specificity, or total error rate.

Clause 14. The computer readable media of any of clauses 4 through 13, wherein serum CH50, C3, and C4 measurements are acquired for one or more new cases whose likelihood of VTE event(s) is to be determined.

Clause 15. The computer readable media of any of clauses 4 through 14, wherein the one or more new cases' measurements are transformed to the derived Dirichlet-transformed, logit-transformed, and log-transformed forms.

Clause 16. The computer readable media of any of clauses 4 through 15, wherein the classification/prediction model is applied to the transformed data of the new cases to obtain estimated classification/prediction of VTE event(s) likelihood.

Clause 17. The computer readable media of any of clauses 4 through 16, wherein an advisory interpretive message regarding the model-generated classification is electronically emitted to the user.

Clause 18. A computer-implemented method for detecting and treating venous thrombosis and venous thromboembolism (VTE) in a human patient, comprising: receiving compliment protein levels for about the patient including CH50, C3, and C4 levels; determining a Dirichlet mixture of CH50 and C3, normalizing the CH50 and C3 derived variables; create logit-transformed CH50 and Log(C4/C3) derived variables; utilizing a logistic regression classification model, apply the classification model to the transformed and derived variables to determine a VTE class and expectancy probability for the patient; based on a comparison of the determined expectancy probability and a threshold, determine that the patient is at risk for VTE when the threshold is satisfied; and initiating an intervening action for the human patient.

Clause 19. The computer-implemented method of clause 18, wherein the logistic regression classification model is determined by: receiving CH50, C4, and C3 information for a population of patients representing a baseline; determining a Dirichlet mixture of CH50 and C3, normalizing the CH50 and C3 derived variables; determining a Dirichlet generalized linear model; creating logit-transformed CH50 and Log(C4/C3) derived variables; utilizing the generalized linear model and the transformed variables, determine a logistic regression classification model; and storing the determined classification model in computer memory thereby enabling the model to be utilized by a smart sensor or decision support tool.

Clause 20. The computer-implemented method of clause 18 or 19, wherein the intervening action comprises at least one of: issuing a notification to a caregiver associated with the patient; automatically scheduling healthcare resources for treating the patient; or modifying a computer program associated with a care plan for the patient.

What is claimed is:

1. A computer system for detecting and treating venous thrombosis and venous thromboembolism (VTE) in a human patient, the system including a processor and a computer memory having instructions stored thereon that when executed cause the processor to perform operations comprising:
    receiving compliment protein levels for a patient including CH50, C3, and C4 levels;
    generating a Dirichlet mixture of the CH50 and C3 levels by normalizing CH50 and C3 values;
    generating a logit-transformed CH50 value and a log-transformed ratio of the C4 and C3 levels;
    generating a VTE class and an VTE expectancy probability for the patient utilizing a logistic regression classification model to classify the patient based on the logit-transformed CH50 value and a log-transformed ratio of the C4 and C3 levels;
    responsive to a comparison of the determined expectancy probability exceeding a threshold, determining that the patient is at risk for VTE; and
    initiating a notification to a caregiver associated with the patient, a scheduling of healthcare resources for treating the patient, or a modification to a computer program associated with a care plan for the patient.

2. A non-transitory computer readable media comprising computer-executable instructions that when executed by a processor cause the processor to implement operations to provide a clinical decision support tool for diagnosing venous thromboembolism (VTE), the operations comprising:
    receiving a baseline data set including a plurality of biomarkers which are interrelated to each other and to known phenotypic VTE status and risk of developing one or more VTE events;
    creating biomarker associations using one or more processors of the computer to adjust for quasi-Dirichlet distributions of the biomarkers' values included in the baseline data set based on a null classification/prediction model configured to identify statistically significant relationships between biomarkers;
    transforming the associated biomarker values as a quasi-Dirichlet mixture, normalizing the range of the derived variables so as to insure that their sum always is equal to 1;
    logit-transforming one of the biomarkers, log-transforming a ratio of two other biomarkers, and determining a classification/prediction model for the VTE dependent variable as a function of the biomarkers' transformed values; and
    based on the classification/prediction model, initiating a notification to a caregiver associated with the patient, a scheduling of healthcare resources for treating the patient, or a modification to a computer program associated with a care plan for the patient.

3. The non-transitory computer readable media of claim 2, wherein the biomarkers comprises quantitative CH50, C3, and C4 measurements of serum from the patient.

4. The non-transitory computer readable media of claim 2, wherein the null model establishes a statistical relation of the covariables to the VTE classifications using logistic regression, Dirichlet regression, support vector machine, neural network, random forest, or gradient boosting.

5. The non-transitory computer readable media of claim 2, wherein the null model is used as an input to determine the statistical significance of relations of the 8 quasi-Dirichlet derived variables to the VTE classification by a method such as a Dirichlet regression or a finite mixture regression model.

6. The non-transitory computer readable media of claim 2, wherein logit-transformation of the raw CH50 values is performed to create an ancillary derived variable.

7. The non-transitory computer readable media of claim 2, wherein log-transformation of the ratio of C4 to C3 is performed to create an ancillary derived variable.

8. The non-transitory computer readable media of claim 2, wherein a classification/prediction model is determined using the derived variables to estimate a likelihood of venous thromboembolic event(s) using logistic regression, support vector machine, gradient boosting, random forest, or neural network.

9. The non-transitory computer readable media of claim 2, wherein the statistical performance quality of the classification/prediction model is determined in terms of sensitivity, specificity, or total error rate.

10. The non-transitory computer readable media of claim 2, wherein serum CH50, C3, and C4 measurements are acquired for one or more new cases whose likelihood of VTE event(s) is to be determined.

11. The non-transitory computer readable media of claim 10, wherein the one or more new cases' measurements are transformed to the derived Dirichlet-transformed, logit-transformed, and log-transformed forms.

12. The non-transitory computer readable media of claim 11, wherein the classification/prediction model is applied to the transformed data of the new cases to obtain estimated classification/prediction of VTE event(s) likelihood.

13. The non-transitory computer readable media of claim 2, wherein an advisory interpretive message regarding the model-generated classification is electronically emitted to the user.

14. The system of claim 1, wherein the logistic regression classification model is determined by generating a baseline Dirichlet mixture using the processor to normalize a plurality of CH50 and C3 values included in a data set comprising CH50, C4, and C3 levels for an identified population.

15. The system of claim 14, wherein the logistic regression classification model is further determined by transforming CH50, C4, and C3 values to generate a baseline logit-transformed CH50 value and a baseline log-transformed ratio of the C4 and C3 levels.

16. The system of claim 14, wherein the operations further comprise generating a logistic regression classification model utilizing a Dirichlet generalized linear model and a plurality of transformed values.

17. The system of claim 16, wherein the operations further comprise storing the generated logistic regression classification model in memory accessible by the processor.

18. The non-transitory computer readable media of claim 2, further comprising accessing a test data set including biomarker values for a patient and transforming the biomarkers of the test data values as a quasi-Dirichlet mixture.

19. The non-transitory computer readable media of claim 18, wherein transforming the biomarkers comprises normalizing the range of the derived variables so as to ensure that their sum always is equal to a predetermined value.

20. The non-transitory computer readable media of claim 19, further comprising: applying the classification/prediction model to determine a resulting state vector $\{y_k\}$; and determining that the patient has a risk for VTS based on the resulting state vector.

21. A computer-implemented method for detecting and treating venous thrombosis or venous thromboembolism (VTE) in a human patient, the method including operations comprising:
- receiving compliment protein levels for a patient including CH50, C3, and C4 levels;
- generating a Dirichlet mixture of the CH50 and C3 levels by normalizing the CH50 and C3 values;
- generating a logit-transformed CH50 value and a log-transformed ratio of the C4 and C3 levels;
- generating a VTE class and a VTE expectancy probability for the patient utilizing a logistic regression classification model to classify the patient based on the logit-transformed CH50 value and a log-transformed ratio of the C4 and C3 levels;
- responsive to a comparison of the determined expectancy probability exceeding a threshold, determining that the patient is at risk for VTE; and
- initiating a notification to a caregiver associated with the patient, a scheduling of healthcare resources for treating the patient, or a modification to a computer program associated with a care plan for the patient.

22. The non-transitory computer readable media of claim 20, further comprising initiating an intervening action based on the risk for VTS, wherein the intervening action includes the notification, the scheduling, or the modification.

23. The method of claim 21, further comprising generating a baseline Dirichlet mixture to normalize a plurality of CH50 and C3 values included in a data set.

24. The method of claim 23, wherein the data set comprises CH50, C4, and C3 levels for a population, and further comprising transforming CH50, C4, and C3 values.

25. The method of claim 24, wherein the transforming generates a baseline logit-transformed CH50 value and a baseline log-transformed ratio of the C4 and C3 levels, and further comprising generating a logistic regression classification model utilizing a Dirichlet generalized linear model and the transformed values.

26. The method of claim 25, wherein the logistic regression classification model is utilized by a smart sensor or decision support tool.

\* \* \* \* \*